(12) United States Patent
Maruyama et al.

(10) Patent No.: US 8,226,682 B2
(45) Date of Patent: Jul. 24, 2012

(54) TISSUE CLOSING DEVICE

(75) Inventors: Tomoji Maruyama, Kanagawa (JP);
Masakatsu Kawaura, Kanagawa (JP);
Ryou Nakamoto, Shizuoka (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 596 days.

(21) Appl. No.: 12/390,008

(22) Filed: Feb. 20, 2009

(65) Prior Publication Data
US 2009/0216266 A1 Aug. 27, 2009

(30) Foreign Application Priority Data

Feb. 21, 2008 (JP) ................................ 2008-040604
Dec. 4, 2008 (JP) ................................ 2008-310206

(51) Int. Cl.
*A61B 17/10* (2006.01)
(52) U.S. Cl. .................... 606/213; 606/151; 606/232
(58) Field of Classification Search .................. 606/213, 606/215, 151, 139, 142, 143, 232
See application file for complete search history.

(56) References Cited

U.S. PATENT DOCUMENTS

| 5,411,520 | A | | 5/1995 | Nash et al. |
| 5,462,558 | A | * | 10/1995 | Kolesa et al. ................. 606/139 |
| 6,712,837 | B2 | * | 3/2004 | Akerfeldt et al. ............. 606/213 |
| 6,860,895 | B1 | * | 3/2005 | Akerfeldt et al. ............. 606/215 |
| 7,850,710 | B2 | * | 12/2010 | Huss ............................. 606/213 |
| 7,875,052 | B2 | * | 1/2011 | Kawaura et al. .............. 606/213 |
| 2003/0060846 | A1 | * | 3/2003 | Egnelov et al. ............... 606/213 |
| 2005/0096697 | A1 | * | 5/2005 | Forsberg et al. .............. 606/213 |
| 2006/0135991 | A1 | * | 6/2006 | Kawaura et al. .............. 606/213 |
| 2006/0241579 | A1 | * | 10/2006 | Kawaura et al. ................. 606/39 |
| 2006/0265008 | A1 | * | 11/2006 | Maruyama et al. ........... 606/232 |
| 2007/0276433 | A1 | * | 11/2007 | Huss ............................. 606/213 |
| 2008/0065121 | A1 | * | 3/2008 | Kawaura et al. .............. 606/146 |
| 2008/0215089 | A1 | * | 9/2008 | Williams et al. .............. 606/215 |
| 2008/0275479 | A1 | * | 11/2008 | Chin et al. .................... 606/153 |
| 2008/0275501 | A1 | * | 11/2008 | Chin et al. .................... 606/213 |
| 2009/0270885 | A1 | * | 10/2009 | Maruyama et al. ........... 606/142 |

FOREIGN PATENT DOCUMENTS

WO  WO 2007/037516 A2  4/2007

OTHER PUBLICATIONS

U.S. Appl. No. 12/067,744, filed Mar. 21, 2008.

* cited by examiner

*Primary Examiner* — Julian Woo
*Assistant Examiner* — Christopher L Templeton
(74) *Attorney, Agent, or Firm* — Buchanan Ingersoll & Rooney PC

(57) ABSTRACT

A tissue closing device includes a closure configured to close a hole penetrating a tissue membrane. The closure has a seal part for covering the hole penetrating the tissue membrane and a peripheral part of the hole from one surface side of the tissue membrane, and a deformable deformation part. The tissue closing device also comprises an arrangement device which removably retains the closure and closes the hole with the closure so as to arrange the closure in a living organism.

16 Claims, 25 Drawing Sheets

TISSUE CLOSING DEVICE

TECHNOLOGICAL FIELD

The present invention relates to a tissue closing device.

BACKGROUND DISCUSSION

Conventionally, minimally invasive operations including insertion of a diagnostic or therapeutic instrument such as a catheter into a living organism tissue such as a blood vessel have been practiced widely. For example, in the treatment of constriction of the coronary artery of the heart, it is necessary for performing the therapeutic treatment to insert an implement such as a catheter into a blood vessel.

Such insertion of a catheter into a blood vessel is usually performed through a puncture formed in a femoral region. After completion of the therapeutic treatment, therefore, it is necessary to staunch the bleeding through the puncture. In this case, since the blood pressure at the time of bleeding from the femoral artery (bleeding blood pressure) is high, severe work such as applying pressure for a relatively long time with a finger of a hand must be performed by a person involved in the medical treatment.

In recent years, in order to perform such a staunching work easily and assuredly, various devices designed to be inserted through the wound hole to close the hole formed in a blood vessel have been developed. An example of such a device is disclosed in U.S. Pat. No. 5,411,520.

The tissue closing device disclosed in the aforementioned patent includes a filament (suture or the like) gripped by a spring-biased ball at the proximal end of the device. When the device is pulled off, the filament slips while tension on the filament is kept constant, and the device is pulled off. Finally, while pulling the filament in the condition where an anchor (anchor member in the blood vessel) is located at the position of the hole formed in the blood vessel, a nonwoven-fabric plug (seal member) is pushed with a pushing-in pipe or tamping member (is compressed with the filament) to compact the plug. In this manner, the hole formed in the blood vessel is sandwiched (clamped) between the anchor and the compacted plug, and is thereby closed.

In this tissue closing device, notwithstanding the advantage that the device can be immediately put to use when required because the plug is compacted in a tube in an assembled condition, there is a concern that since the plug is kept compacted in the tube very tightly during storage, a load is exerted on the plug and so the plug may show a semi-permanently set shape.

Besides, particularly in the case where a portion corresponding to the plug is composed of a deformable frame-like member, the frame-like member stored for a long time in the state of being put under a load will tend to acquire a semi-permanently set shape (i.e., will undergo plastic deformation). Consequently, it would be difficult to deform the frame-like member for the purpose of embedding it in a living organism, or an excessive force would be needed to effect the deformation.

SUMMARY

The tissue closing device disclosed here is configured so that until the device is put to use, exertion of a load on a deformation part of a closure can be prevented or restrained. At the time of using the device, the deformation part of the closure can be retained at a distal portion of an elongated part of an arrangement device relatively easily and quickly.

A tissue closing device includes: a closure for closing a hole penetrating a tissue membrane, the closure having a seal part for covering a hole penetrating a tissue membrane and a peripheral part of the hole from one surface side of the tissue membrane, and a deformable deformation part. An arrangement device removably retains the closure and closes the hole with the closure so as to arrange the closure in a living organism. The arrangement device includes an elongated part which has in a distal portion thereof an opening part capable of retaining the deformation part of the closure and which is capable of penetrating the hole. A retaining member is located at the distal portion of the elongated part in an initial condition and retains the closure and of which a part or the whole part is movable relative to the elongated part toward the proximal side. A part or the whole part of the retaining member is moved relative to the elongated part toward the proximal side, whereon the deformation part of the closure is pushed into the opening part, thereby making a transition from a condition in which the closure is retained by the retaining member to a condition in which the deformation part of the closure is retained at a distal portion of the elongated part.

The retaining member includes an accommodating part having a wide space part provided therein with a space, a narrow space part provided on the distal side relative to the wide space part and provided therein with a space narrower than the space of the wide space part, and a transition part provided between the wide space part and the narrow space part and provided therein with a space. The closure is contained in the wide space part or in the wide space part and the transition part in the initial condition, and is inserted into the narrow space part when the retaining member is moved relative to the elongated part toward the proximal side.

The transition part has an inclined surface, and the closure is gradually folded along the inclined surface when the retaining member is moved relative to the elongated part toward the proximal side.

The seal part is plate-shaped, and the seal part is gradually inclined along the inclined surface when the closure is folded.

The tissue closing device includes a sheath having a connector at a proximal portion thereof, and is used with the elongated part inserted in a lumen of the sheath and with the sheath mounted to the arrangement device.

The retaining member and the connector have a first connecting part for connection between the retaining member and the connector, and the connector and the retaining member are connected to each other, so that the sheath is moved together with the retaining member relative to the elongated part toward the proximal side when the retaining member is moved relative to the elongated part toward the proximal side.

The arrangement device includes a proximal part provided on the proximal side of the elongated part; the retaining member and the proximal part have a second connecting part for connection between the retaining member and the proximal part, and the retaining member is moved relative to the elongated part toward the proximal side so as to effect connection between the retaining member and the proximal part.

The retaining member has a tubular part which is projectingly formed at a distal portion of the retaining member and of which a lumen communicates with the space in the narrow space part. The tubular part is inserted into the connector to effect communication between the lumen of the tubular part and the lumen of the sheath when the connector of the sheath and the retaining member are connected to each other And the closure retained at a distal portion of the elongated part is passed through the lumen of the tubular part to be inserted into the lumen of the sheath when the retaining member is moved relative to the elongated part toward the proximal side.

The tubular part is so configured that the resistance at the time of passage of the closure through the lumen of the tubular part is greater than the resistance at the time of passage of the closure through the narrow space part, and the deformation part is pushed into the opening part when the closure is passed through the lumen of the tubular part.

The closure is inserted into the narrow space part, the load exerted on the deformation part in a radial direction of the elongated part is increased, and the deformation part is compressed in a radial direction of the elongated part as compared with its state in the initial condition.

The closure in its folded state has the deformation part pushed into the opening part.

The retaining member includes a compressing part by which the deformation part of the closure is compressed in a radial direction of the elongated part as compared with its state in the initial condition, and a part which is located on the distal side relative to the compressing part and which folds the seal part of the closure.

The retaining member includes a proximal-side member, and a distal-side member disposed on the distal side of the proximal-side member and movable relative to the proximal-side member, the distal-side member has a compressing part by which the deformation part of the closure is compressed in a radial direction of the elongated part as compared with its state in the initial condition as the distal-side member is moved relative to the proximal-side member.

The compressing part clamps the deformation part from both sides of the deformation part. When the distal-side member is moved relative to the proximal-side member toward the proximal side, the compressing part clamps the deformation part from both sides of the deformation part, whereby the deformation part is compressed in a radial direction of the elongated part as compared with its state in the initial condition, and the deformation part is pushed into the opening part.

The compressing part has a pair of clamp pieces capable of being deformed toward and away from each other, and the pair of clamp pieces clamp the deformation part therebetween when deformed toward each other.

The distal-side member has a pair of leg parts which are disposed to face each other with a center axis of the elongated part therebetween and are elastically deformable, and the pair of clamp pieces are provided at proximal portions of the pair of leg parts.

The proximal-side member has a pair of inclined surfaces capable of making contact with the pair of clamp pieces, and the pair of clamp pieces are deformed along the pair of inclined surfaces toward each other to clamp the deformation part therebetween when the distal-side member is moved relative to the proximal-side member toward the proximal side.

The proximal-side member has, on the proximal side of the pair of inclined surfaces, a clamping state retaining part for retaining the condition in which the deformation part is clamped between the pair of clamp pieces, and the condition of clamping the deformation part between the pair of clamping pieces is retained by the clamping state retaining part and the deformation part is pushed into the opening part when the distal-side member is moved relative to the proximal-side member toward the proximal side.

The proximal-side member has, on the proximal side of the clamping state retaining part, a compression canceling part for accommodating the pair of clamp pieces, and the pair of clamp pieces are contained into the compression canceling part, the pair of clamp pieces are deformed away from each other by resilient forces of the pair of leg parts to release the deformation part.

Preferably, the pair of clamp pieces are provided at a pair of elastically deformable leg parts.

Movement inhibitive means inhibits the pair of clamp pieces contained in the compression canceling part from returning into the clamping state retaining part. The seal part is plate-like in shape, and the deformation part is in the shape of a frame deformable between a first form in which the deformation part is expanded in a direction substantially perpendicular to the seal part and contracted in a direction substantially parallel to the seal part and a second form in which the deformation part is contracted in the direction substantially perpendicular to the seal part and expanded in the direction substantially parallel to the seal part.

According to the device disclosed here, in the initial condition (the condition immediately upon assemblage), the deformation part of the closure is not retained at the distal portion of the elongated part of the arrangement device. Therefore, exertion of a load on the deformation part can be prevented or restrained during the period until the tissue closing device is put to use (e.g., during storage or the like). Accordingly, the deformation part (closure) can be prevented from acquiring a semi-permanently set shape or from being deteriorated or broken.

At the time of use, by moving the retaining member relative to the elongated part of the arrangement device toward the proximal side, the deformation part of the closure can be retained at the distal portion of the elongated part easily and speedily, whereby the tissue closing device can be put into a usable condition.

DETAILED DESCRIPTION

Figure 1:
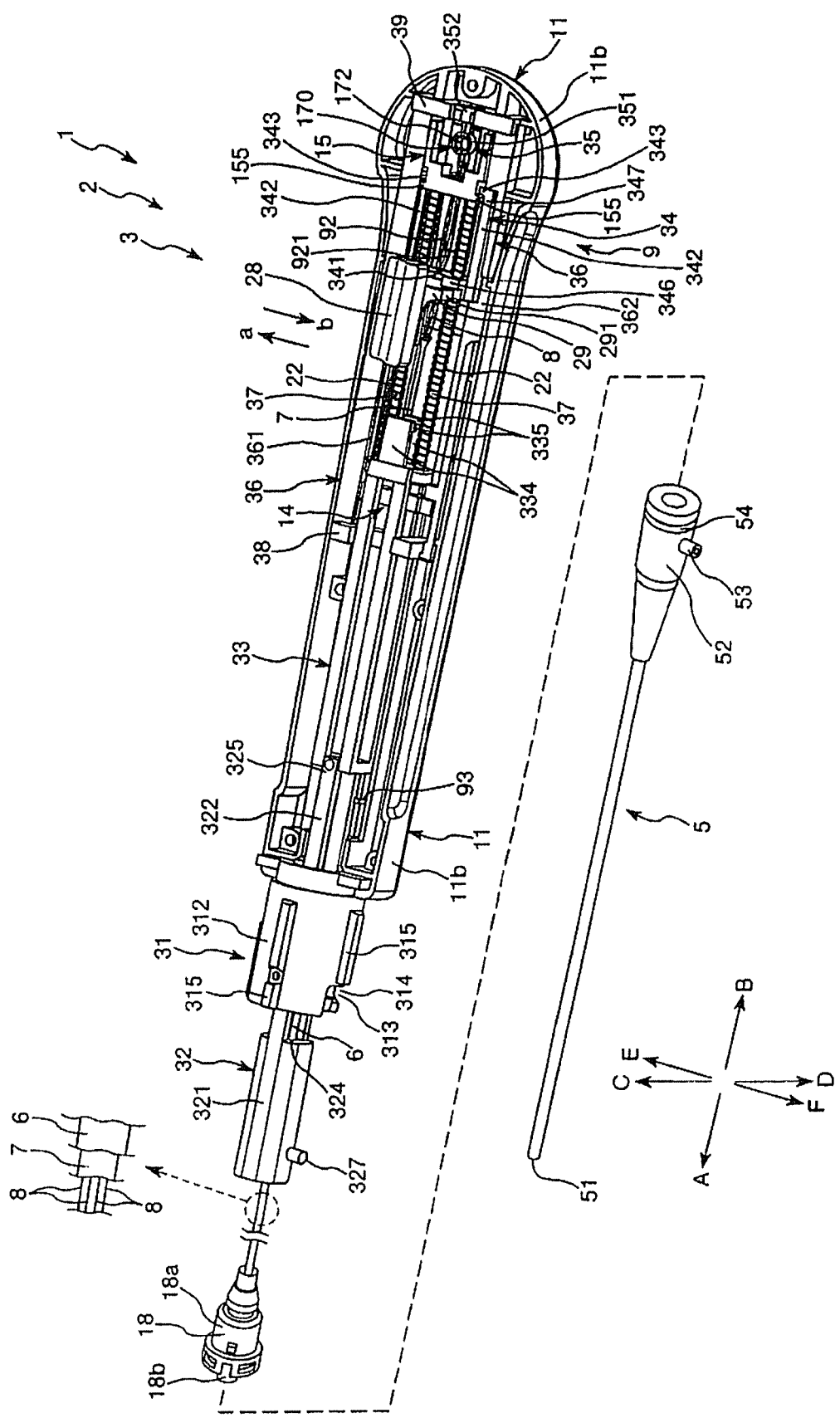
FIG. 1 is a perspective view of a first embodiment of the tissue closing device disclosed here.

Set forth below is a description of a first embodiment of the tissue closing device disclosed here. By way of explanation, FIGS. 1 and 12A to 18B the illustration of the upper cover of the casing is omitted for purposes of facilitating an understanding of aspects of the tissue closing device. In addition, with respect to the rail on one side (on the side of arrow F), the inside thereof is shown. In FIG. 1, the inside of the cover tube and the inside of the fixing tube in the area surrounded by the broken-line circle are shown in an enlarged form. Additionally, in FIG. 10, the cover tube and the fixing tube are individually drawn in broken lines. At 7 in FIG. 11C, the fixing tube is drawn in broken lines. In FIGS. 12A to 18B, except for a part thereof, an illustration of the thread is omitted to avoid complicating the illustrations.

For convenience of description, in FIGS. 1, 2, 7 to 10, and 12A to 18B, the direction of arrow A is referred to as the "distal" direction, the direction of arrow B is referred to as the "proximal" direction, the direction of arrow C is referred to as the "upward (upper)" direction, and the direction of arrow D is referred to as the "downward (lower)" direction. In FIGS. 3-5 and 11A-11D, the upper side is referred to as the "proximal side" and the lower side is referred to as the "distal side."

The tissue closing device 1 disclosed here is a device for closing (closing up) an undesirable hole formed in a tissue membrane, for example a living organism lumen (such as a blood vessel), an internal organ, or an internal tissue of a living organism and which penetrates percutaneously (a wound hole penetrating a tissue membrane).

Figure 2:
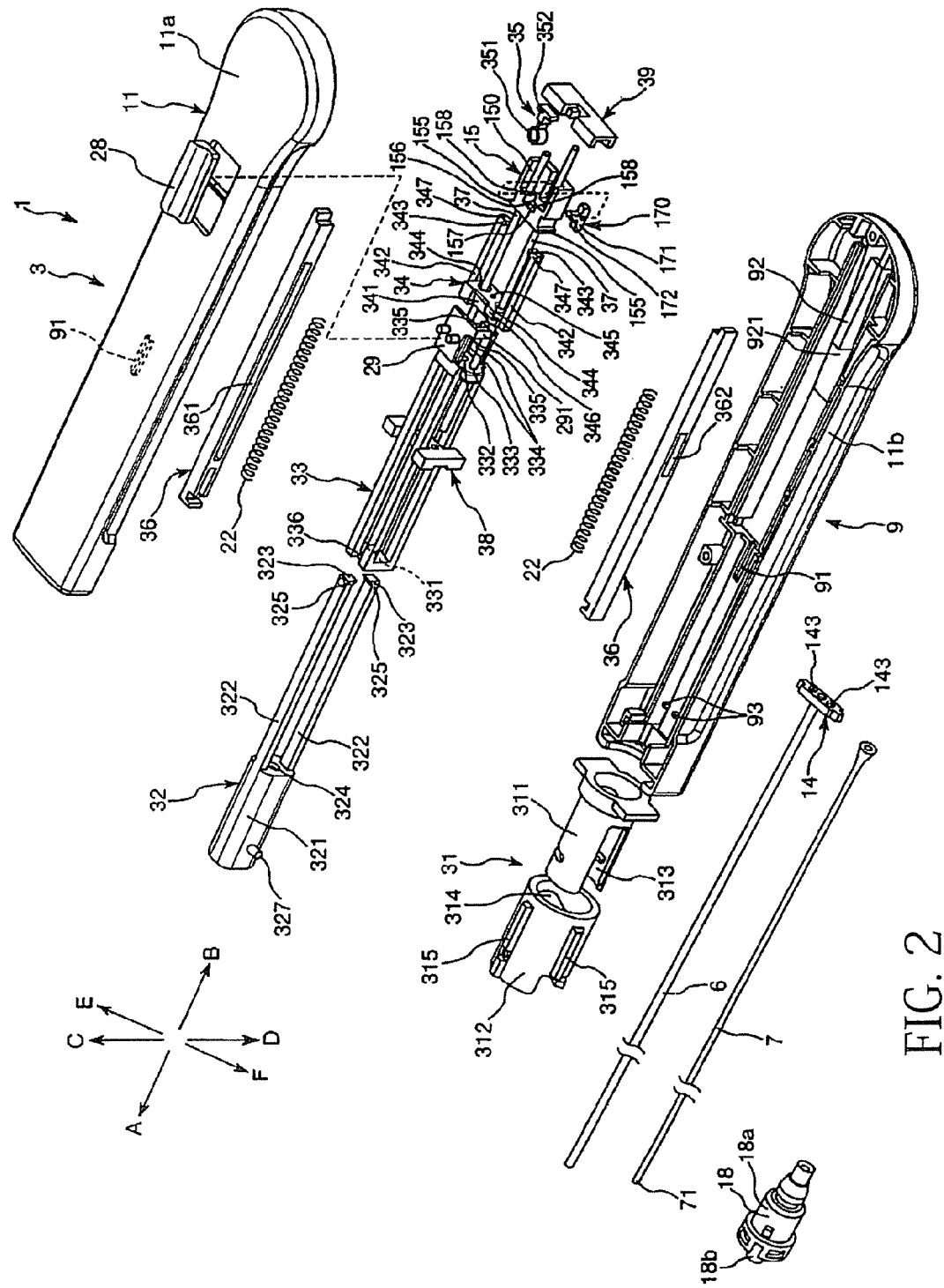
FIG. 2 is an exploded perspective view showing parts or components of an arrangement device of the tissue closing device shown in FIG. 1.
Figure 3:
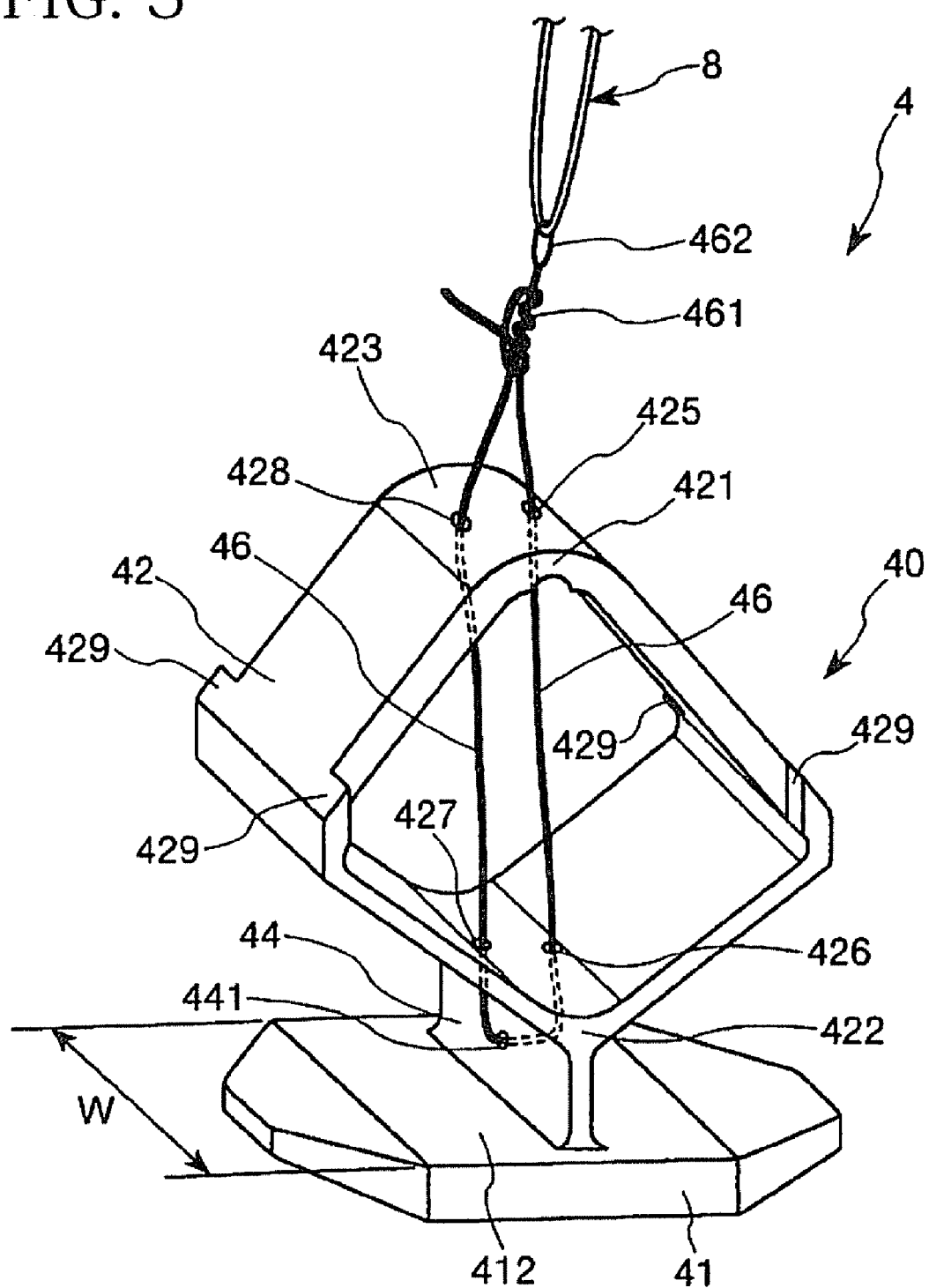
FIG. 3 is a perspective view of a closure forming a part of the tissue closing device shown in FIG. 1.

As shown in FIGS. 1, 2 and 3, the tissue closing device 1 includes an elongated arrangement device (i.e., feeding and deformation means) 3 and a clip 4. The elongated arrangement device 3 possesses a distal portion sized to pass through a wound hole penetrating a tissue membrane, and a proximal part 9 on the proximal side. The clip 4 serves as a closure (i.e., tissue closure) and is removably retained (i.e., joined) at the distal portion of the arrangement device 3. The clip 4 is sized and configured, or otherwise operative, to close the wound hole penetrating the tissue membrane.

The clip 4 includes a clip body (i.e., closure body) 40 and a thread (i.e., first filamentous element) 46 serving as a fixing part. The clip body 40 is composed of a seal part 41, a deformable deformation part 42, and a connecting part 44 connecting the seal part 41 and the deformation part 42 to each other. In addition, the thread 46 has a knot 461 and a loop 462. Additional details associated with the clip 4 will be described in more detail later.

The arrangement device 3 is used by being inserted in, or being removably mounted in, a sheath (elongated tubular element) 5 possessing a centrally extending through-hole (lumen) 51 extending along the sheath in the axial direction. That is, the arrangement device 3 is used such that the sheath 5 is removably mounted to the arrangement device 3 as generally shown in FIGS. 13A and 13B. The sheath 5 and the arrangement device 3 constitute an elongated body part 2. At the time of a staunching (hemostatic) operation (i.e., during a procedure to close a wound hole), the distal portions of the sheath 5, the distal portion of the arrangement device 3, and the clip 4 are passed through the wound hole. In other words, they are inserted through the wound hole into a living body lumen such as a blood vessel.

The sheath 5 is substantially cylindrical in shape, and has a proximal portion at which is provided a hub (connector) 52. In addition, a hemostatic valve (valve body) formed as a slit is disposed on the inner peripheral side of the hub 52. The side portion of the hub 52 is provided with a port part (projection) 53 possessing a lumen (passage) communicating with the through-hole 51.

A groove 54 is provided at the outer peripheral portion of the proximal portion of the hub 52. The groove 54 is formed along the circumferential direction once over the entire circumference.

Examples of the sheath 5 which can be used include a sheath (introducer sheath) left indwelling after a treatment in therapy (PCI (Percutaneous Coronary Intervation)) or diagnosis (CAG (Coronary Angiography)) carried out by use of a catheter. Alternatively, a sheath for exclusive use with the tissue closing device 1 may be used.

The description above notes that the sheath 5 is included in the components of the body part 2 in this embodiment. However, it is also possible to adopt a configuration in which the sheath 5 is not included in the components of the body part 2.

The arrangement device 3 includes: a second filamentous element 8 which is detachably connected to the clip 4 (the thread 46 of the clip 4) and which retains the clip 4 (the thread 46 of the clip 4); a cover member or cover means 6 for covering other parts of the device 3 and possessing a distal portion sized and configured to penetrate a wound hole; an anchoring member or anchoring means 7 for providing an anchor and possessing a distal portion capable of penetrating a wound hole; a retaining member (inserter) 18 located at a distal portion of the cover tube 6 in the initial condition (the condition immediately upon assembly), accommodating (retaining) the clip 4 and movable along the cover tube 6 toward the proximal side (in the proximal direction); and a proximal part 9 provided on the proximal side of the fixing tube 7 and the cover tube 6. The illustrated embodiment shows that the second filamentous element 8 can be in the form of a thread, the cover member or cover means 6 can be in the form of an elongated first tubular member, and the anchoring member or anchoring means 7 can be in the form of an elongated second tubular member.

The retaining member 18 is configured to effect a transition, at the time of moving toward the proximal side, from a condition in which the clip 4 is retained by the retaining member 18 to a condition in which the deformation part 42 of the clip 4 is retained in the opening part 61 (distal portion) of the cover member 6 by pushing the deformation part 42 into the opening part 61 of the cover member 6. The retaining member 18 will be described in more detail below. In this embodiment, the retaining member 18 and the cover member 6 are preferably configured so that relative movement between the two members 6, 18 is possible, and this condition is expressed as the retaining member 18 is movable relative to the cover member (cover tube) 6 or as the cover tube 6 is movable relative to the retaining member 18. When the retaining member 18 is moved relative to the cover member 6 toward the proximal side, for example, only the retaining member 18 may be moved, only the cover member 6 may be moved, or both the retaining member 18 and the cover member may individually be moved. In the present embodiment shown and described as an example, the description is set forth based on the assumption that the retaining member 18 is moved toward the proximal side.

The clip 4 (the thread 46 of the clip 4) is detachably retained at a distal portion of the arrangement device 3 by the thread 8. In addition, the clip 4 (the thread 46 of the clip 4) is contained and retained in the retaining member 18 until the retaining member 18 is moved toward the proximal side from the initial condition. The thread 8 retains (holds) the clip 4 in such a manner that a portion of the deformation part 42 on the opposite side (distal side) from the seal part 41 can be moved (displaced) relative to a portion on the seal part 41 side (base portion side) (proximal side) of the deformation part 42.

The fixing tube 7 is disposed in the lumen of the cover tube 6 in a concentric manner, and the cover tube 6 is movable (slidable) relative to the fixing tube 7 in the longitudinal direction of the two tubes. The cover tube 6 and the fixing tube 7 are positioned in the through-hole 51 of the sheath 5 at the time of mounting the sheath 5. The proximal part 9 is provided on the proximal side of the fixing tube 7 and the cover tube 6.

The fixing tube 7 is formed of a comparatively hard material. The cross-sectional shape of the fixing tube 7 is substantially elliptic (like a flattened circle) at a distal portion 71 of the fixing tube 7, and is substantially circular on the proximal side relative to the distal portion 71.

Figure 10:
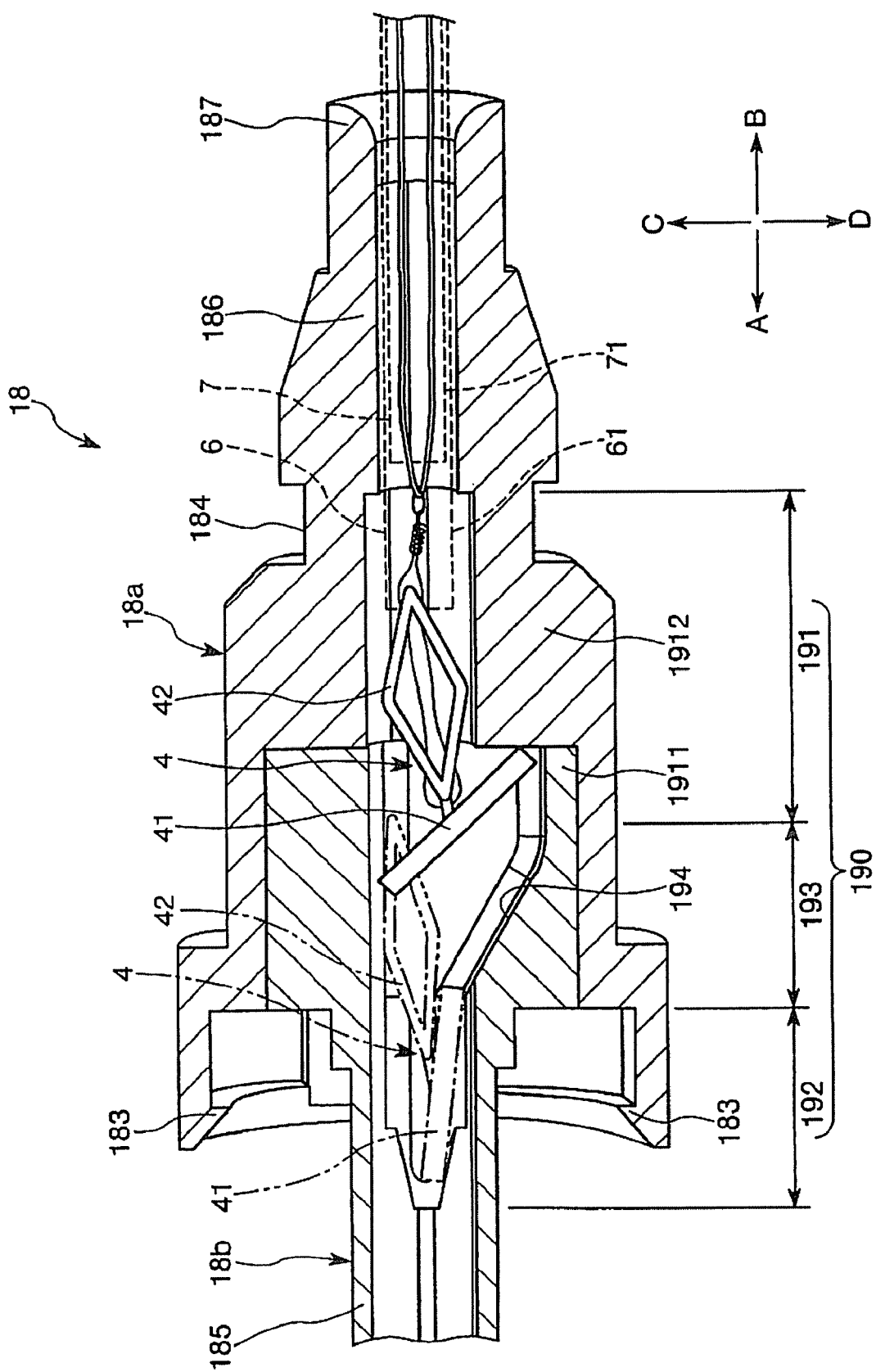
FIG. 10 is a cross-sectional view showing the retaining member shown in FIG. 8.

FIG. 10 generally shows the cover tube 6 provided at its distal portion with the opening part 61 into which the deformation part 42 of the clip 4 can be inserted and positioned, and in which the deformation part 42 can be removably retained (mounted). The opening part 61 is located on the distal side relative to the distal end of the fixing tube 7. The cross-sectional shape of the cover tube 6 is substantially elliptic (like a flattened circle) at a distal portion of the cover tube 6, or at the opening part 61. The adjoining portion of the cover tube 6 on the immediate proximal side of the distal portion (at a portion corresponding to the distal portion 71 of the fixing tube 7) possesses a cross-sectional shape corresponding to the distal portion 71 of the fixing tube 7, namely it is substantially elliptic. Further proximal of this adjoining portion of the cover tube 6, the cover tube 6 possesses a cross-sectional shape that is substantially circular.

In addition, the thread 8 is disposed in the lumen of the fixing tube 7, and is movable relative to the fixing tube 7 in the longitudinal direction of the fixing tube 7.

When the cover tube 6 and the fixing tube 7 of the arrangement device 3 have been inserted into the through-hole 51 from the proximal side of the sheath 5, and the sheath 5 is located on the most proximal side, the opening part 61 of the cover tube 6 is exposed from the distal end of the sheath 5 (the distal-most end of the sheath 5 is located on the proximal side of the distal end or distal-most end of the cover tube 6 so that the distal end portion of the cover tube 6 is disposed distally beyond the distal-most end of the sheath 5), and the distal end of the sheath 5 is located on the proximal side relative to the distal end of the fixing tube 7.

The cover tube 6 covers the outer surface of the fixing tube 7, and the opening part 61 of the cover member 6 covers at least part of the deformation part 42 of the clip 4.

The fixing tube (fixing means) 7 functions such that when the thread 46 of the clip 4 is pulled in the proximal direction by the thread 8, the knot 461 of the thread 46 of the clip 4 is anchored at the distal portion 71 of the fixing tube 7, and, further, the deformation part 42 is locked through the knot 461 (indirectly locked), so that the deformation part 42 can be deformed by tightening the thread 46 through relative movement of the knot 461 in the distal direction.

As shown in FIGS. 1 and 2, the proximal part 9 includes: a casing (main body) 11; a cover tube support part (cover tube support member) 14 supporting the cover tube 6; a thread support part (retaining member support part) 15 supporting the thread 8; coupling means 170 for detachably coupling the thread 8 to the thread support part 15; a first charge member 32; a second charge member 33; coupling means 34 for detachably coupling the thread support part 15 and the second charge member 33 to each other; actuatable members 22; a pair of guide bars 37; a lever 28; a lock part 29 joined to the lower side of the lever 28; and a stopper 35. In the illustrated embodiment, the coupling means 170 is in the form of a pin which is turnably disposed at the thread support part 15 to detachably couple the thread 8 to the thread support part 15, the coupling means 34 is in the form of a slide coupling member, and the actuatable members 22 are elastic members in the form of a pair of springs (coil springs) 22. Also in this embodiment, the first charge member 32 and the second charge member 33 constitute charge means.

The casing 11 includes an upper cover 11*a* located on the upper side, and a lower cover 11*b* located on the lower side and joined to the upper cover 11*a*. The casing has a tubular shape (prismatic shape) which is roughly rectangular parallelepiped in outside shape, and is rounded on the proximal side.

A connector 31 is provided at a distal portion of the casing 11. A base portion 321 of the first charge member 32 (described later) is fixed to the connector 31. The connector 31 serves as a mechanism for mounting the sheath 5 to the proximal part 9 (casing 11), that is as a mechanism for fixing the sheath 5 to the casing 11 through the retaining member 18 and the base portion 321 of the first charge member 32. The connector 31 is composed of an inner tube part 311 in which is positioned the base portion 321, and an outer tube part 312 disposed at the outer periphery of the inner tube part 311 so as to be turnable (rotatable) in the circumferential direction. That is, the inner tube part 311 is positioned in the outer tube part 312.

The peripheral wall of the inner tube part 311 is provided with a rectilinear slot 313 opened at the distal end, and the peripheral wall of the outer tube part 312 is provided with a helical slot 314 opened at the distal end. The outer tube part 312 can be rotated relative to the inner tube part 311 in a predetermined direction until a distal portion of the slot 314 in the outer tube part 312 coincides with a distal portion of the slot 313 in the inner tube part 311, and can be rotated in the direction reverse to the predetermined direction until a proximal portion of the slot 314 coincides with a proximal portion of the slot 313.

In addition, a plurality of ribs 315 are provided on the outer peripheral surface of the outer tube part 312. The ribs 315 act as finger hook parts at the time of operation and are positioned at regular or equal intervals (regular or equal angular intervals). In the illustrated embodiment, four ribs 315 are provided.

As illustrated in FIG. 2, grooves 91 are provided at a central portion of the casing 11, specifically on the inner side of the upper cover 11a and on the inner side of the lower cover 11b. The grooves 91 receive proximal portions 325 of rod-like elements 322 of the first charge member 32 (described later). The grooves 91 are oriented in the longitudinal direction of the arrangement device 3 (casing 11) so that the grooves 91 on the inner side of the upper cover 11a face the grooves 91 on the inner side of the lower cover 11b.

A rib 92 is provided at the proximal portion of the casing 11, on the inner side of the lower cover 11b. The rib 92 extends along the longitudinal direction of the arrangement device 3 (casing 11), and a stepped portion 921 is formed on the distal side of a distal portion of the rib 92.

At a distal portion of the casing 11 and on the inner side of the lower cover 11b, a pair of projections 93 are formed. The first charge member 32 (described later) is so configured that, with a proximal portion of a base portion 321 of the first charge member 32 abutting the pair of projections 93, the first charge member 32 is inhibited from moving in the proximal direction beyond the projections 93.

Further, a guide bar support part 38 is provided (e.g., fixed) at a central portion of the inside of the casing 1, while a guide bar support part 39 is provided (e.g., fixed) at a proximal portion of the inside of the casing 11.

Two guide bars 37 are disposed between the guide bar support part 38 and the guide bar support part 39. Distal portions of the guide bars 37 are each held (supported) by the guide bar support part 38, and proximal portions of the guide bars 37 are each held (supported) by the guide bar support part 39. The guide bars 37 extend in the longitudinal direction of the arrangement device 3 (casing 11) and are parallel to each other.

In the illustrated embodiment, the guide bars 37 are each composed of a pipe (tube), but the guide bars are not limited in this regard. For example, the guide bars 37 may each be a solid (non-hollow) bar.

In addition, at side portions of the inside of the casing 11, two rails 36 are provided (e.g., fixed) and extend from the guide bar support part 38 to the guide bar support part 39. The rails 36 extend in the longitudinal direction of the arrangement device 3 (casing 11) and are parallel to each other.

The rails 36 are each provided with a groove 361 extending in the longitudinal direction (axial direction) of the rail. The grooves 361 are positioned at the inside surfaces of the rails 36 so that the groove 361 of one rail faces the groove 361 of the other rail 36.

Bottom portions (side walls) of the grooves 361 of the rails 36 are provided with hole portions 362 into which proximal portions 347 of corresponding rod-like elements 342 of the slide coupling member 34 (described later) are inserted or positioned at the time of actuation (restoring) of the pair of coil springs 22 (described later). The hole portion 362 on each rail 36 is located near the central portion of the rails 36.

The first charge member 32, the second charge member 33, the guide bar support part 38, the slide coupling member 34, and the thread support part 15 are disposed inside the casing 11 to be movable relative to the casing 11 in the longitudinal direction of the arrangement device 3 (casing 1).

In the disclosed embodiment, the first charge member 32, the second charge member 33, the slide coupling member 34, and the thread support part 15 are disposed in this order from the distal side toward the proximal side. The second charge member 33 is so disposed that the guide bar support part 38 is located between a distal portion and a proximal portion of the second charge member 33.

In addition, the cover tube support part 14 is located between the guide bar support part 38 and a proximal portion of the second charge member 33.

The base portion 321 of the first charge member 32 is located on the distal side relative to the connector 31 as shown in FIG. 1.

The slide coupling member 34 is composed of a base portion 341 and a pair of rod-like elements 342 projecting in the proximal direction from both side portions of the base portion 341.

Claws 343 are located or erected at proximal portions 347 of the rod-like elements 342. The claws 343 face each other and project inwards.

The base portion 341 is provided with a pair of hole portions 344 through which the pair of guide bars 37 pass.

The central portion of the base portion 341 is provided with a hole portion 345 through which the thread 8 passes.

Further, the base portion 341 is provided with an upwardly projecting projection 346 which is locked with a projected portion 291 of the lock part 29.

As shown in FIGS. 1-6B, projections 155 exist at both side portions of a distal portion of the thread support part 15. The projections 155 are adapted to engage the corresponding claws 343 of the slide coupling member 34.

In addition, the thread support part 15 is provided, on the proximal side relative to a distal portion thereof, with a recess 150. The recess 150 opens on the upper side and at the proximal end of the thread support part 15.

The distal portion of the thread support part 15 includes a pair of hole portions 156 through which the thread 8 passes. Further, a hole portion 157 is provided between the pair of hole portions 156 in the distal portion of the thread support part 15. The thread 8 is adapted to pass through the hole portion 157.

In addition, the thread support part 15 is provided in its distal portion with a pair of hole portions 158 through which to pass the pair of guide bars 37. The pin 170 is composed of a base portion 171 and an upstanding projection 172 at a central portion of the base portion 171.

The pin 170 is so disposed that it can be turned at its base portion 171 relative to the thread support part 15, and can thereby assume an erect state in which the projection 172 (pin 170) is vertically upright and a leveled state in which the projection 172 (pin 170) is leveled or horizontally oriented. With the lower surface (back-side surface) of the base portion 171 in contact with the upper surface of the rib 92 of the casing 1, the pin 170 is retained in the erect state. The pin 170 is disposed in the recess 150 of the thread support part 15.

The stopper 35 is composed of a C-shaped stopper body 351 which is provided with a gap on the distal side (is open on the distal side), and a support part 352 for supporting the stopper body 351. The support part 352 is disposed (fixed) at the guide bar support part 39. The projection 172 of the pin 170 is inserted in the stopper body 351 of the stopper 35. As a result, the thread support part 15 is held (locked) by the stopper 35 through the pin 170, whereby the thread support part 15 is inhibited from moving. In other words, the pin 170 and the thread support part 15 are inhibited by the stopper 35 from moving relative to the casing 11 in the distal direction.

In addition, at least the stopper body 351 of the stopper 35 is configured to have an appropriate hardness and to be elastically deformable. The length of the gap (gap distance) on the distal side of the stopper body 351 is smaller than the diameter of the projection 172 of the pin 170.

This helps ensure that movement of the thread support part 15 is inhibited until a force exerted on the thread support part 15 (pin 170) through the thread 8, namely a pulling force with which the thread support part 15 is pulled in the distal direction through the thread 8, exceeds a predetermined threshold (predetermined value). It is also helps ensure that, when the force exceeds the threshold, the projection 172 of the pin 170 is released via the gap in the stopper body 351 so that the thread support part 15 can move in the distal direction relative to the casing 11. In this case, as will be described later, with the thread support part 15 (the thread support part 15, the slide coupling member 34 and the second charge member 33) enabled to move in the distal direction, it becomes possible to cancel the restraint by which the coil springs 22 are retained in the compressed state (deformed state, or active state). In other words, the canceling of the restraint which restrains the coil springs 22 in the compressed state is made possible on condition that the force exerted on the thread support part 15 has exceeded the predetermined threshold.

The threshold is preferably about 150 to 1500 gf, more preferably about 200 to 1000 gf.

As a result, even if the clip 4 is caught to some extent inside a blood vessel or the like before the seal part 41 of the clip 4 comes securely into contact with a wound hole and the surrounding tissue, the clip 4 can be expected to be released before the pin 170 comes off the stopper 35 (i.e., before the lock is canceled). Accordingly, the clip 4 can be moved to the wound hole so as to bring the seal part 41 into contact with the wound hole and the surrounding tissue. In addition, the pin 170 can be expected to come off from the stopper 35 (i.e., the lock is canceled) before the wound hole and the surrounding tissue are excessively pulled in the proximal direction by the clip 4. Accordingly, the seal part 41 can be relatively safely and assuredly brought into contact with the wound hole and the surrounding tissue.

The thread 8 is composed of a double thread (double filamentous element) in which a single thread (filamentous element) is folded back to form a fold-back portion 81 at one end portion thereof. In addition, the thread 8 is attached to the thread support part 15 in such a manner that the thread 8 is passed through each of the hole portions 156 as a single thread, is once wound around a distal portion of the thread support part 15, and then both end portions of are tied together.

In the condition where the thread is passed through the clip 4 (the loop 462 of the thread 46 of the clip 4) and folded back at a distal portion of the arrangement device 3 so as to retain the clip 4, the thread 8 is passed through the hole portion 157 of the thread support part 15, Further, the fold-back portion 81 is hooked on the projection 172 of the pin 170 so that the fold-back portion 81 is detachably coupled to the thread support part 15 by the pin 170. The other end portion (an end portion on the opposite side from the fold-back portion 81) is attached to the thread support part 15 as mentioned above.

The overall outer shape of the second charge member 33 is substantially tetragonal prismatic (rectangular parallelepiped) basket-like (frame-like).

The distal portion of the second charge member 33 is provided with a hole portion 331 through which the cover tube 6 passes.

In addition, the proximal portion of the second charge member 33 is provided with a pair of hole portions 333 through which the pair of guide bars 37 pass. Further, the proximal portion of the second charge member 33 is provided, between the pair of hole portions 333, with a hole portion 332 through which the fixing tube 7 passes.

A proximal portion of the second charge member 33 is provided with a pair of projected portions 334. The projected portions 334 project in the proximal direction from an upper portion and a lower portion of the proximal portion are erectly provided. The proximal portion of each of the projected portions 334 is provided with a claw 335. The claws 335 are oriented to face each other and project inwardly to the inner side. The pair of claws 335 engage the base portion 341 of the slide coupling member 34.

The second charge member 33 is provided with two recesses 336. The recesses 336 are positioned at the upper portion and lower portion of a distal portion of the second charge member 33.

The first charge member 32 is composed of a base portion 321, and a pair of rod-like elements 322 projecting in the proximal direction from an upper portion and a lower portion of a proximal portion of the base portion 321.

Positioned at the proximal portions 325 of the rod-like elements 322 are projected portions 323 which face each other and project inwardly towards each other and to the inner sides. Each of the projected portions 323 engages one of the recesses 336 in the distal portion of the second charge member 33.

Figure 7:
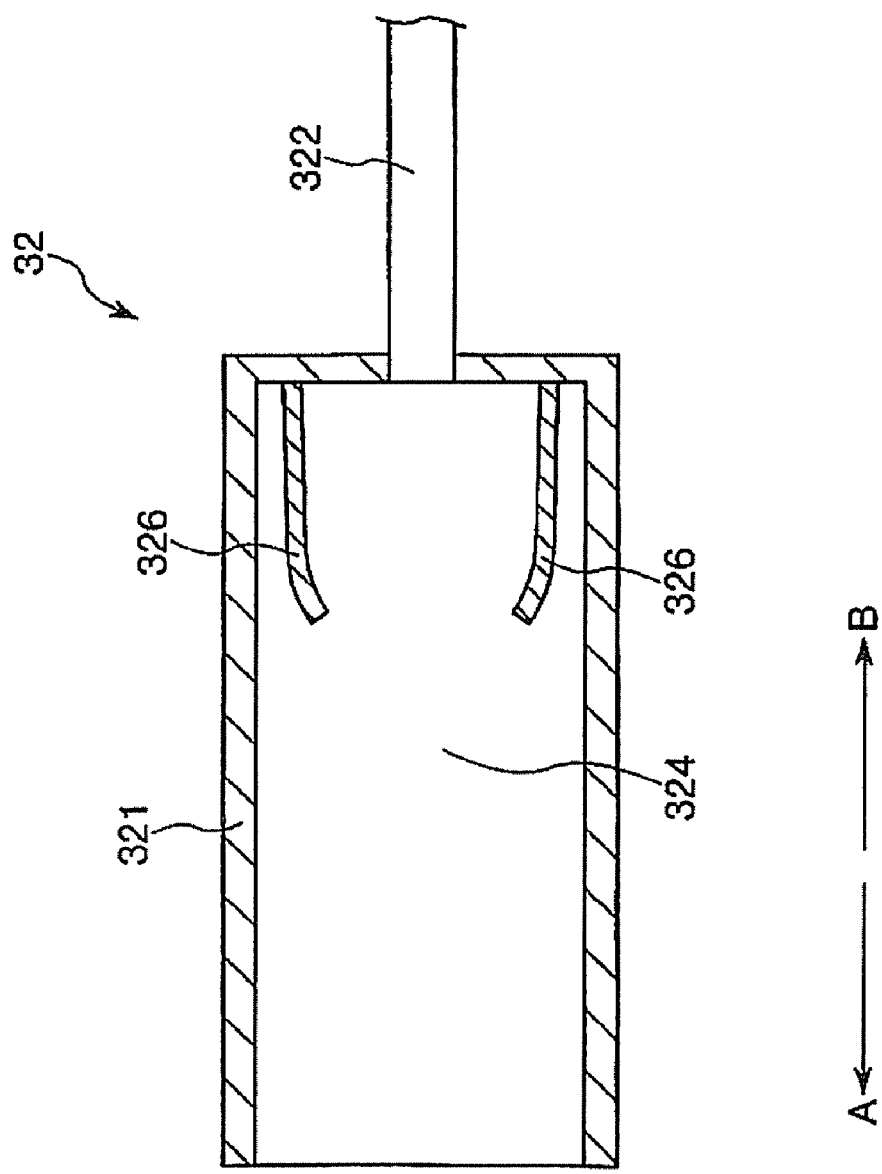
FIG. 7 is a cross-sectional view of a base portion of a first charge member of the tissue closing device shown in FIG. 1.

In addition, as shown in FIG. 7, the central portion of the base portion 321 of the first charge member 32 is provided with a hole portion 324 through which the cover tube 6 passes and in which the retaining member 18 is positioned. A pair of claws 326 is positioned in the hole portion 324.

An outside surface (outer peripheral surface) of the base portion 321 is provided with a projection 327 projecting sideways. The projection 327 is disposed at a position corresponding to the slot 313 in the inner tube part 311. Here, in the condition where the position of a distal portion of the slot 313 in the inner tube part 311 of the connector 31 and the position of a distal portion of the slot 314 in the outer tube part 312 coincide with each other, when the first charge member 32 is moved in the proximal direction to insert the base portion 321 into the inner tube part 311, in such a manner that the projection 327 of the base portion 321 is located at the distal portion of the slot 313 in the inner tube part 311 and the distal portion of the slot 314 in the outer tube part 312, and the outer tube part 312 is rotated in a predetermined direction (in the example shown, counterclockwise as viewed from the distal direction), the projection 327 is pushed in the proximal direction by an edge portion fronting on the slot 314 of the outer tube part 312 and is gradually moved in the proximal direction along the slot 313 in the inner tube part 311. As a result, the base portion 321 is fixed to the casing 11.

The cover tube support part 14 includes a pair of hole portions 143 through which pass the pair of guide bars 37. A proximal portion of the cover tube 6 is fixed (supported) to the cover tube support part 14 at a position between the pair of hole portions 143 of the cover tube support part 14.

In addition, a proximal portion of the fixing tube 7 positioned in the cover tube 6 is fitted (fixed) to the base portion 341 of the slide coupling member 34.

The outer diameter of the main body of the fixing tube 7 is smaller than the inner diameter of the hole portion 332 in the base portion of the second charge member 33.

The two guide bars 37 pass through the pair of hole portions 333 in the second charge member 33, the pair of hole portions 143 in the cover tube support part 14, the pair of hole portions 344 in the slide coupling member 34, and the pair of hole portions 158 in the thread support part 15. Further, the side portions of the cover tube support part 14 and the pair of rod-like elements 342 of the slide coupling member 34 are positioned in respective grooves 361 in the pair of rails 36.

As a result, the second charge member 33 and the thread support part 15 are guided by the guide bars 37 along the longitudinal direction (axial direction) of the guide bars 37.

In addition, the cover tube support part 14 and the slide coupling member 34 are guided by the guide bars 37 and the rails 36 along the longitudinal direction (axial direction) of the guide bars 37 and the rails 36.

In the initial condition shown in FIG. 1 (the condition immediately upon assembly), the pair of projected portions 323 of the first charge member 32 engage the pair of recesses 336 in the distal portion of the second charge member 33. This helps ensure that the first charge member 32 and the second charge member 33 move together as a single unit.

In this initial condition, the pair of projections 155 at the distal portion of the thread support part 15 engage the pair of claws 343 of the slide coupling member 34. This helps ensure that the slide coupling member 34 and the thread support part 15 move together as a single body. It should be noted here that, strictly speaking, movement of the slide coupling member 34 and the thread support part 15 is inhibited by the stopper 35 and the lock part 29.

In addition, in the initial condition, the second charge member 33 and the slide coupling member 34 are spaced from each other by a predetermined distance. This helps ensure that movement of the first charge member 32 and the second charge member 33, and movement of the slide coupling member 34 and the thread support part 15, takes place individually.

As will be described later, in the charged condition at the time of use as shown in FIGS. 12A to and 13B (in the condition where the coil springs 22 are kept in the contracted state, i.e., the active state), the pair of claws 335 of the second charge member 33 engage the base portion 341 of the slide coupling member 34, whereas the pair of recesses 336 in the distal portion of the second charge member 33 and the pair of projected portions 323 of the first charge member 32 are disengaged from each other. This helps ensure that the second charge member 33, the slide coupling member 34, the thread support part 15 and the fixing tube 7 move together as a single unit, and the thread support part 15 is inhibited from moving relative to the fixing tube 7 (moving in the proximal direction)

The members for connecting the clip 4, the thread support part 15 and the casing 11 along the longitudinal direction of the arrangement device 3 do not include any member that expands and contracts in the longitudinal direction of the arrangement device 3, such as a spring. Therefore, in the charged condition, the distance between the clip 4 and the casing 11 is kept constant (inclusive of substantially constant) until the force exerted on the thread support part 15 through the thread 8 exceeds the above-mentioned predetermined threshold.

In addition, the two coil springs 22 are disposed around the pair of guide bars 37, respectively. The coil springs 22 pass through the hole portions 344 in the slide coupling member 34, and are located between the proximal portion of the second charge member 33 and the distal portion of the thread support part 15. The distal ends of the coil springs 22 contact the proximal portion of the second charge member 33 whereas the proximal ends of the coil springs 22 contact the distal portion of the thread support part 15. In the initial condition, each of the coil springs 22 is in a natural state (where no external force is applied to the springs) or in a slightly contracted state.

The lever 28 is an operating member for carrying out the following switching operations. In the initial condition, the lever 28 is operative to effect switching between a condition where movement of the slide coupling member 34 and the thread support part 15 relative to the casing 11 or vice versa is inhibited (locked condition) and a condition where such relative movement is permitted (unlocked condition). In the charged condition, the lever 28 is operative to effect switching between a condition where movement of the second charge member 33, the slide coupling member 34, the thread support part 15, the fixing tube 7 and the pair of coil springs 22 relative to the casing 11 or vice versa is inhibited (locked condition) and a condition where such relative movement is permitted (unlocked condition).

The lever 28 is disposed on the upper outside surface of the upper cover 11a of the casing 11 so that it can be moved or operated (slid) in the directions of the arrows a and b in FIGS. 1 and 2.

The lock part 29 is joined to the lower side of the lever 28 so that the lever 28 and the lock part 29 move together as a single unit. The lock part 29 is located on the inside of the upper cover 11a of the casing 11. In addition, a downwardly projecting projected portion 291 is provided as a portion of the lock part 29.

When the lever 28 is located in the locking position shown in FIGS. 1 and 2, the projected portion 291 of the lock part 29 contacts the distal side of the projection 346 of the slide coupling member 34 so that the projection 346 is locked by the projected portion 291, whereby the slide coupling member 34 is inhibited from moving in the distal direction. Specifically, the slide coupling member 34 is locked by the lock part 29 in the following manner. In the initial condition, movement of the slide coupling member 34 and the thread support part 15 in the distal direction is inhibited. In the charged condition, movement of the second charge member 33, the slide coupling member 34, the thread support part 15, the fixing tube 7 and the coil springs 22 in the distal direction is inhibited, whereby an operation for actuating the coil springs 22 is prohibited.

In addition, when the lever 28 is moved in the direction of arrow b in FIG. 1 (located in an unlocking position), the projected portion 291 of the lock part 29 is moved (retracted) to the lateral side relative to the projection 346 of the slide coupling member 34 (to a position where the projection 346 is absent), whereby the projection 346 is unlocked from the projected portion 291. As a result, movement of the slide coupling member 34 in the distal direction is permitted on condition that the inhibition by the stopper 35 of the thread support part 15 from moving is canceled (the locking is canceled). In other words, the locking of the slide coupling member 34 by the lock part 29 is canceled. Consequently, in the charged condition, on condition that the inhibition by the stopper 35 of the thread support part 15 from moving is canceled, movement of the second charge member 33, the slide coupling member 34, the thread support part 15, the fixing tube 7 and the coil springs 22 in the distal direction is permitted, whereby an operation for actuating the coil springs 22 is permitted.

The lever 28 and the lock part 29 constitute switch means for switching between a locked condition where an operation for actuating the pair of coil springs (actuatable members) 22 by trigger means is prohibited and an unlocked condition where the operation is permitted.

Now, the clip 4 will be described below. As shown in FIG. 3, the clip (closure) 4 includes the clip body (closure body) 40 and the thread (first filamentous element) 46 serving as a fixing part.

The clip body 40 is composed of the seal part 41, the deformable deformation part 42, and the connecting part 44 connecting the seal part 41 and the deformation part 42. Preferably, the seal part 41, the deformation part 42 and the connecting part 44, namely, the clip body 40 is an integrally formed, one-piece member entirely made of the same material.

The seal part 41 is a member having a flat surface portion (flat surface) 412 brought into secure contact with a wound hole and a peripheral portion (a portion including the wound hole in a tissue membrane) from one side surface (inside surface) of the tissue membrane to cover the wound hole and the peripheral portion of the wound hole. The seal part 41 is preferably plate-shaped.

The surface of the seal part 41 to be connected to the deformation part 42 (the upper surface on the upper side in FIG. 3) is a substantially flat surface. In addition, the seal part 41 can rock about the location where the connecting part 44 is provided. In this way, the angle of the seal part 41 relative to the deformation part 42 can be changed.

The deformation part 42 has a shape similar to a pantograph composed of a substantially rhombic frame body, and is coupled (connected) to a central portion (e.g., center) of the flat surface portion 412 of the seal part 41 through the connecting part 44.

Specifically, the deformation part 42 has a frame-shape deformable between a first form in which the deformation part 42 is expanded in a direction perpendicular to the seal part 41 and contracted in a direction parallel to the seal part 41, and a second form in which the deformation part 42 is contracted in the direction substantially perpendicular to the seal part 41 and expanded in the direction substantially parallel to the seal part 41. The deformation part 42 can be deformed into an any desired form or configuration (position) between the first form and the second form, such as a basic form (basic shape) (natural state) shown in FIG. 3, a form permitting passage of the deformation part 42 through a wound hole, a form permitting the deformation part 42 to close a wound hole by clamping the tissue membrane between the seal part 41 and itself from the side of the other surface (outside surface) of the tissue membrane, etc.

In the case where the tissue membrane is a blood vessel wall (living body lumen wall), the one-side surface is that surface of the blood vessel wall (living body lumen wall) which is distal from the body surface, i.e., the inside surface, and the other-side surface is that surface of the blood vessel wall (living body lumen wall) which is proximal from the body surface, i.e., the outside surface.

Here, in the present embodiment, the deformation part 42 is formed by bending a belt-shaped member four times into a tetragonal annular shape (bending a belt-shaped member a plurality of times into a polygonal annular shape). Specifically, the deformation part 42 has a tetragonal shape (tetragonal frame-like shape) having four links formed integrally and four corner (intersection) portions which can be bent in a hinge-like manner. With respect to the two corner portions 421, 422 located at diagonal positions in the vertical direction in FIG. 3, the corner portion 422 on the lower side in FIG. 3 (the seal part 41 side) is coupled to a substantially central portion of the flat surface portion 412 of the seal part 41 through the connecting part 44, and serves as an immobile portion which cannot be moved relative to the end portion, on the upper side in FIG. 3, of the connecting part 44.

This makes it possible for the deformation part 42 to be deformed so that the corner portion 421 and the corner portion 422 are displaced toward and away from each other, i.e., to be contracted and expanded in two directions orthogonal to each other, and also to rock (pivot) relative to the seal part 41.

The upper surface (the surface on the opposite side from the seal part 41) 423 of the corner portion 421 on the upper side in FIG. 3 (on the opposite side from the seal part 41) is a curved bulging surface. The corner portion 421 of the deformation part 42 (an end portion, on the opposite side from the seal part 41, of the deformation part 42) is provided near its center with two holes (through-holes) 425, 428, and the corner portion 422 is provided near its center with two holes (through-holes) 426, 427.

Portions of the deformation part 42 on the upper side of the two corner portions located at diagonal positions in the left-right direction in FIG. 3 have both side portions cut out in elongated shape so that four stepped portions 429 are formed. When the deformation part 42 is pushed into the opening part 61 of the cover tube 6, the distal end of the cover tube 6 abuts on the stepped portions 429. This serves as a way of controlling the amount of insertion of the deformation part 42 into the opening part 61 of the cover tube 6. As a result, when the clip 4 is folded, the seal part 41 can be inclined (put into a lying state) to a larger extent, whereby the clip 4 can be made more compact.

Further, the connecting part 44 is plate-shaped, and is provided near its center with a hole (through-hole) 441. By virtue of the connecting part 44, the seal part 41 and the corner portion 422 of the deformation part 42 are spaced from each other by a predetermined distance.

Figure 4:
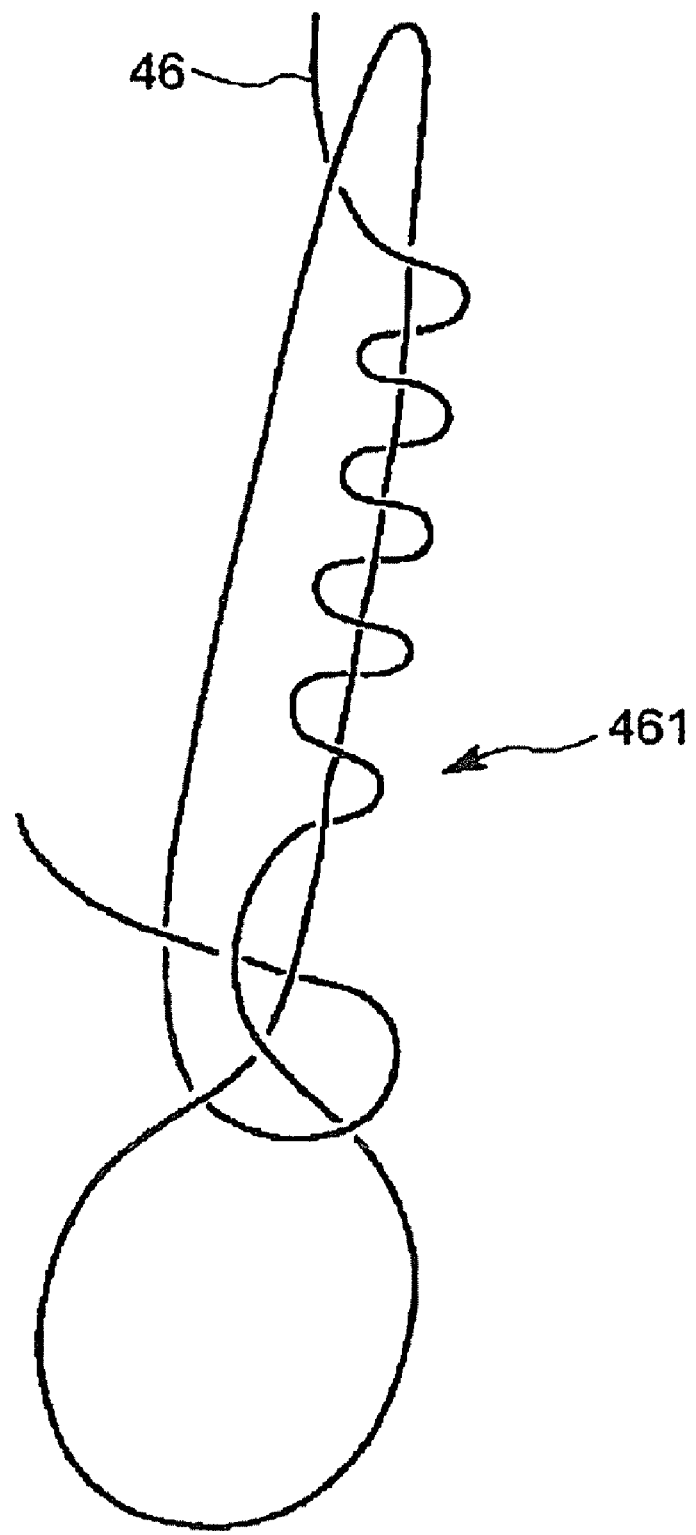
FIG. 4 is an illustration of one example of a knot in the closure of the tissue closing device shown in FIG. 1.
Figure 5:
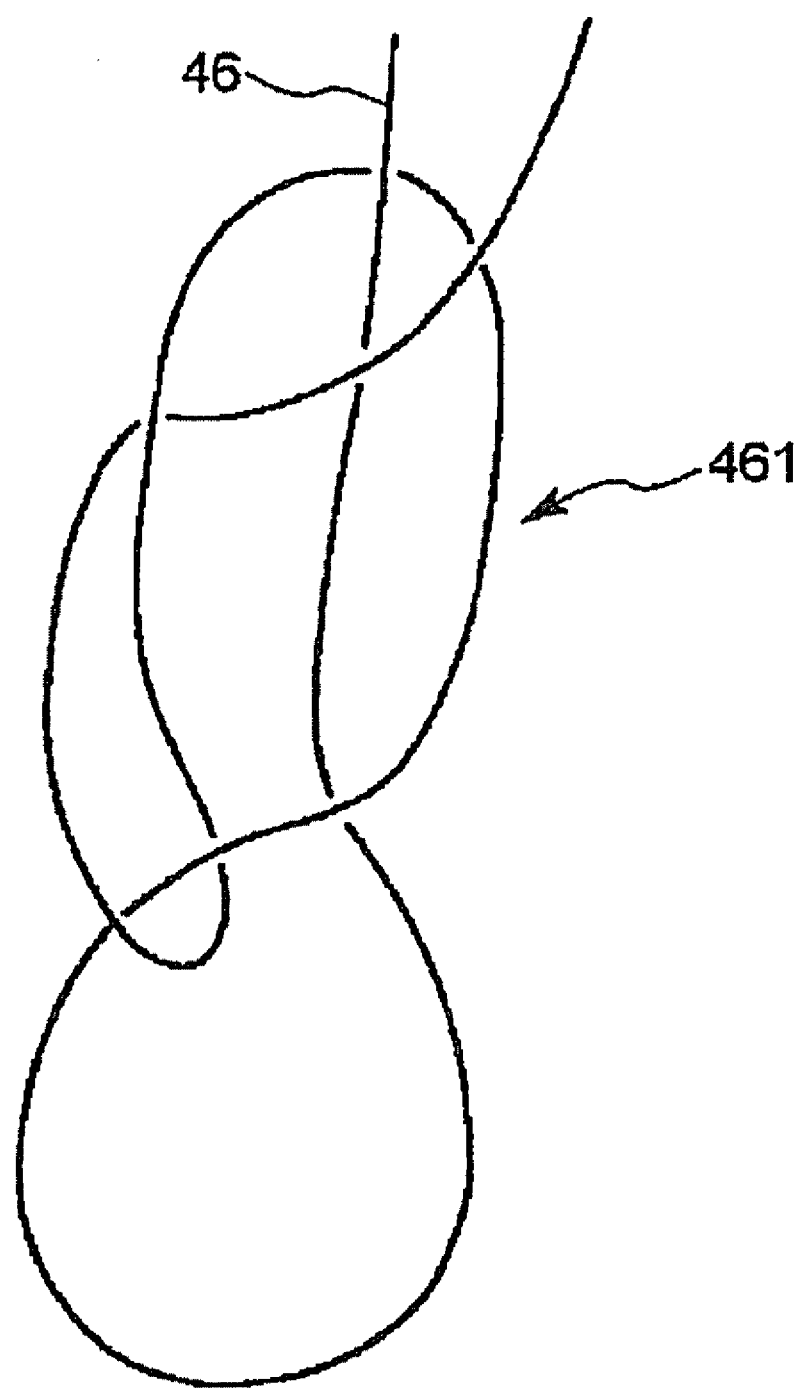
FIG. 5 is an illustration of another example of the knot in the closure of the tissue closing device shown in FIG. 1.
Figure 6:
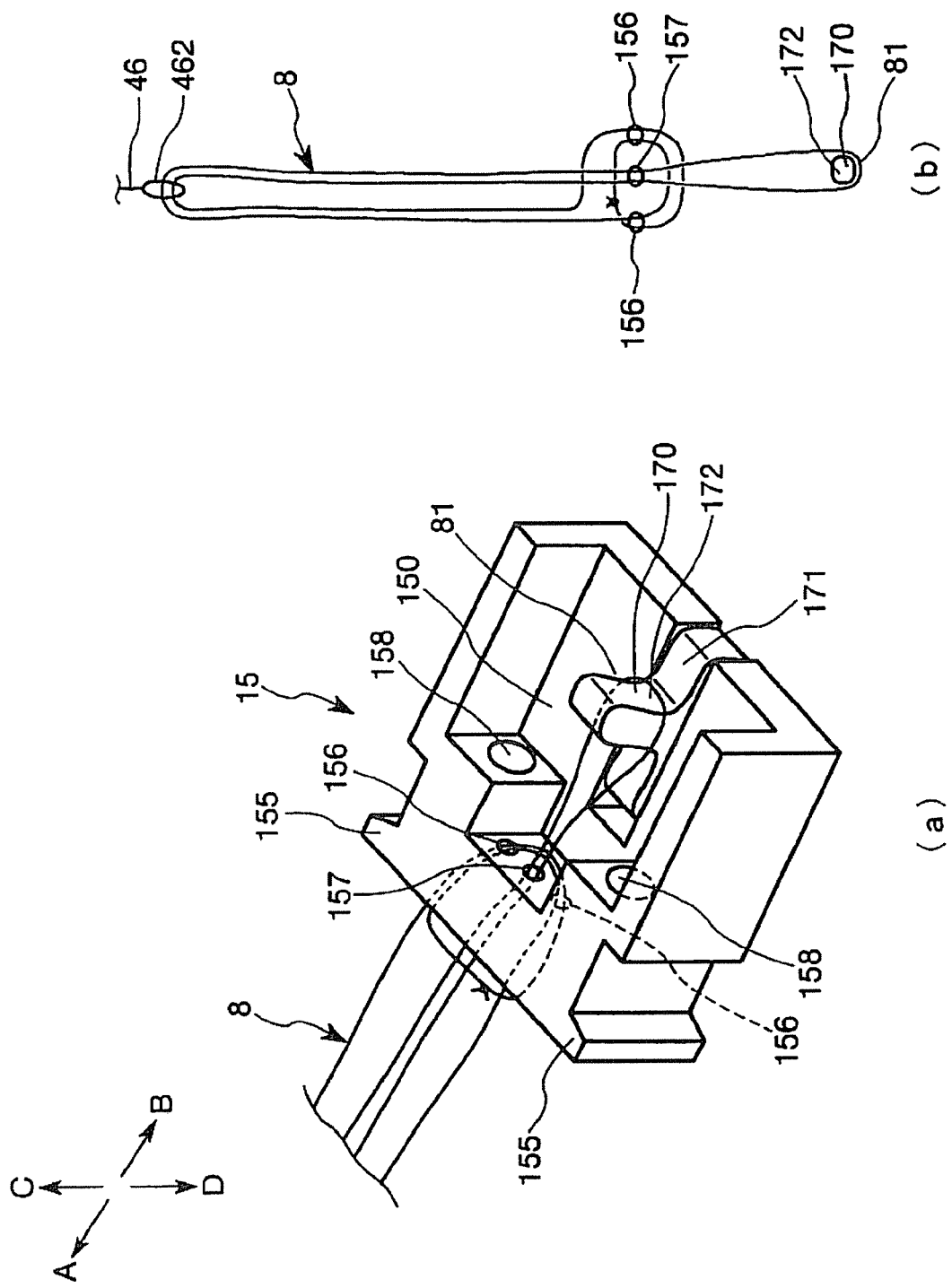
FIGS. 6A and 6B show a thread support part, a pin and a thread of the tissue closing device shown in FIG. 1.

The thread 46 is hooked on the side of an end portion of the deformation part 42 (the opposite side from the seal part 41) and the side of an end portion of the deformation part 42 (on the side of the seal part 41) so that the thread 46 is attached to the clip body 40. In the present embodiment, the thread 46 is hooked on the corner portion 421 of the deformation part 42 (the end portion of the deformation part 42, on the opposite side from the seal part 41) and the connecting part 44 in the state of penetrating the corner portion 421 of the deformation part 42 and the connecting part 44. The thread 46 passes sequentially through the hole 425 in the corner portion 421 of the deformation part 42, through the hole 426 in the corner portion 422, through the hole 441 in the connecting part 44, through the hole 427 in the corner portion 422, and through the hole 428 in the corner portion 421, before forming the knot 461 in a shape as shown in FIG. 4 or 5 on the corner portion 421 side, outside the deformation part 42. Such a knot is called "clinch knot." In addition, as shown in FIG. 3, a loop 462 through which the thread 8 passes is formed on the upper side of the knot 461.

The knot 461 is formed so as to be movable in the distal direction, namely toward the lower side in FIG. 3. With the knot 461 moved on the thread 46 in the distal direction so as to tighten the thread 46, the deformation part 42 can be deformed into a predetermined form between the first form and the second form, and can be kept or maintained in this state. When the thread 46 is positioned to retain the condition where the deformation part 42 is in the predetermined form, the knot 461 is located at the end portion of the deformation portion 42, on the opposite side from the seal part 41 (i.e., at the corner portion 421). Since the knot 461 is strongly fastened on the thread 46, the knot 461 is not naturally moved in the proximal direction unless a strong force is exerted on the knot.

The knot 461 is larger than the inner diameter of the fixing tube 7, whereas the loop 462 is smaller than the inner diameter of the fixing tube 7. This helps ensure that when the knot 461 of the thread 46 of the clip 4 is moved by the fixing tube 7 to tighten the thread 46 and deform the deformation part 42, the loop 462 can be brought into the lumen of the fixing tube 7 and that the knot 461 can be prevented from entering the lumen of the fixing tube 7. Therefore, the knot 461 can be reliably moved. Thus, the thread 46 functions as a fixing part for fixing the form or configuration of the deformation part 42.

As has been described above, the thread 8 passes through the lumen of the fixing tube 7 while also passing through the loop 462 of the thread 46.

The thread 46 may serve also as the thread 8. In this case, a method may be adopted in which, after the deformation part 42 is fixed by the thread 46, the thread 46 is cut by a pair of scissors or the like on the proximal side relative to the knot 461.

In addition, a configuration may be adopted in which the thread 46 is composed of a double thread (double filamentous element) in which a single thread (filamentous element) is folded back to form a fold-back portion at one end, and the fold-back portion forms the loop 462.

At least a part of the clip body 40 of the clip 4 is preferably formed of a bioabsorbable material. It is particularly preferable that a major part of the clip body 40 (most of the clip body) as a whole is integrally formed of a bioabsorbable material. This helps ensure that the major part of the clip body 40 is absorbed into a living body after a predetermined period of time, without remaining in the living body. This eliminates its influence on the human body. The thread 46 also is preferably formed of a bioabsorbable material.

Examples of the bioabsorbable material which can be used here include polylactic acid, polyglycolic acid, polydioxanone, etc., which may be used either singly or together as a composite material.

The material constituting the clip body 40 of the clip 4 is not limited to the bioabsorbable material. for example, a biocompatible material such as biocompatible resins and metals can be used. The material constituting the thread 46 is also not limited to the bioabsorbable material.

As for the physical properties of material required for the clip body 40 of the clip 4, especially for the deformation function of the deformation part 42, excellent hinge characteristics are desirable. Specifically, materials having a tensile strength of 250 to 500 Kg/cm$^2$, an elongation of 150 to 800%, a tensile modulus of 8 to 20×103 Kg/cm2, and a bending strength of 300 to 700 Kg/cm$^2$ are preferable. When these physical property values are satisfied, the clip body 40 possesses excellent hinge characteristics, and the deformation part 42 can have a desired deformability.

As shown in FIGS. 11A-11D, when the thread 46 of the clip 4 is pulled in the proximal direction by the thread 8 in the condition where the deformation part 42 of the clip 4 is released from the distal portion of the cover tube 6 and the deformation part 42 is therefore deformable, the knot 461 of the thread 46 of the clip 4 is locked by the distal portion 71 of the fixing tube 7. Further, the deformation part 42 is locked through the knot 461 (locked indirectly), whereby the knot 461 is moved in the distal direction, the thread 46 is tightened, and the deformation part 42 is deformed.

Figure 11:
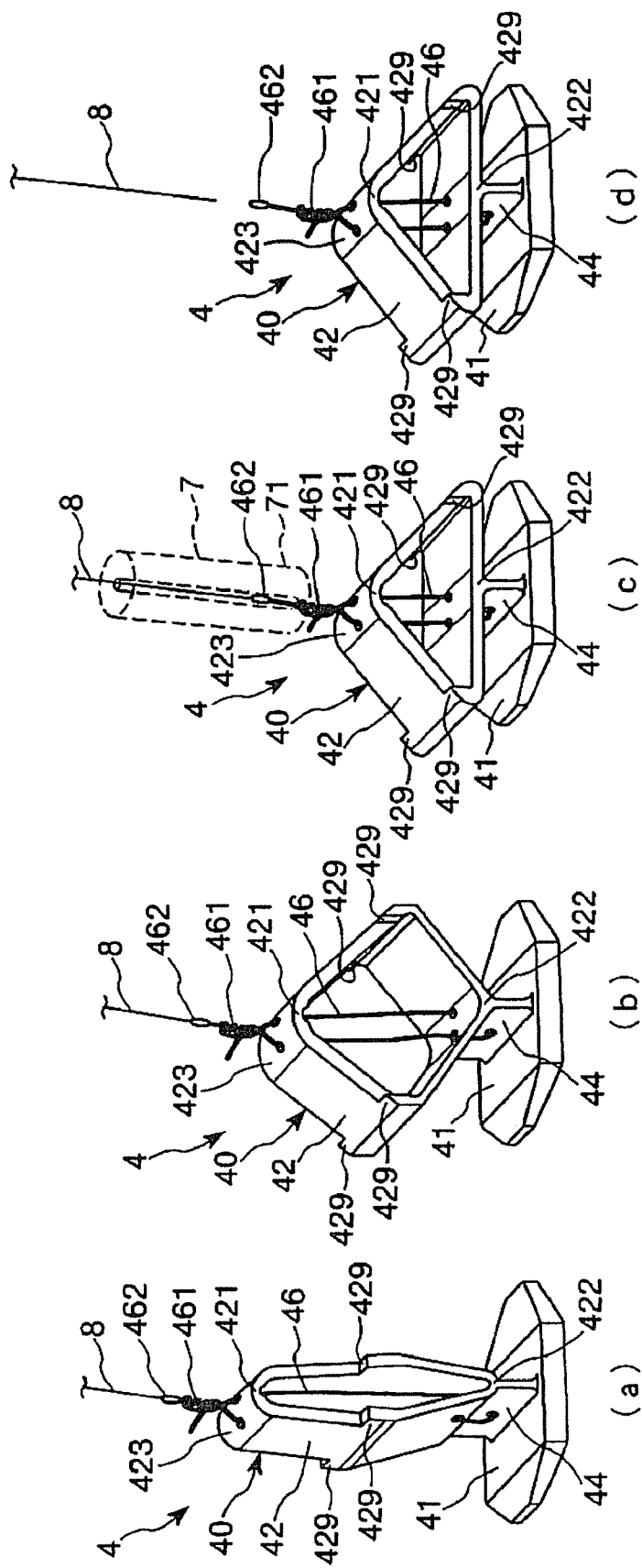
FIGS. 11(a)-11(d) are perspective views illustrating operational aspect of the tissue closing device shown in FIG. 1.
Figure 12:
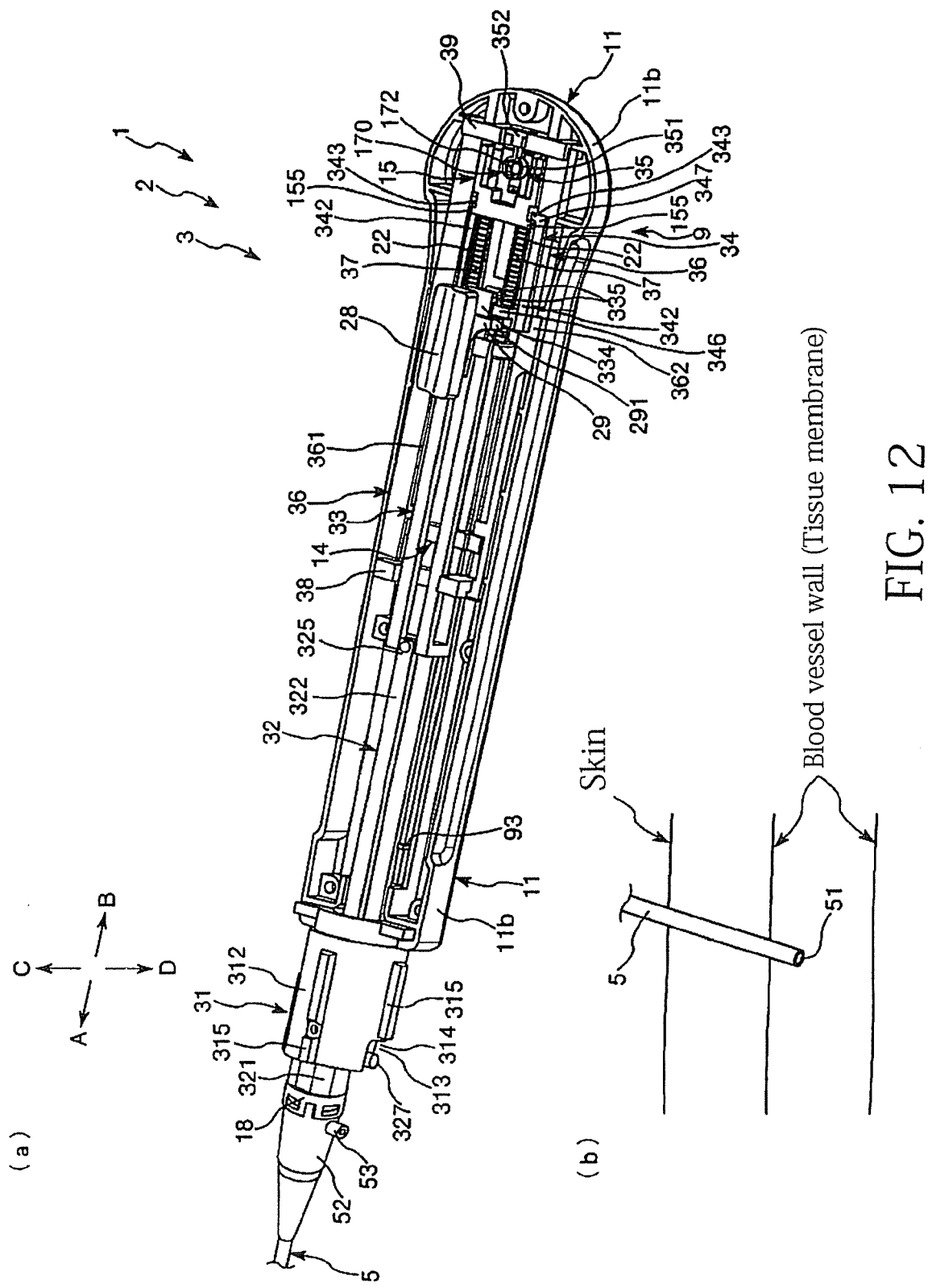
FIGS. 12(a) and 12(b) are perspective views depicting other operational aspect of the tissue closing device shown in FIG. 1.
Figure 13:
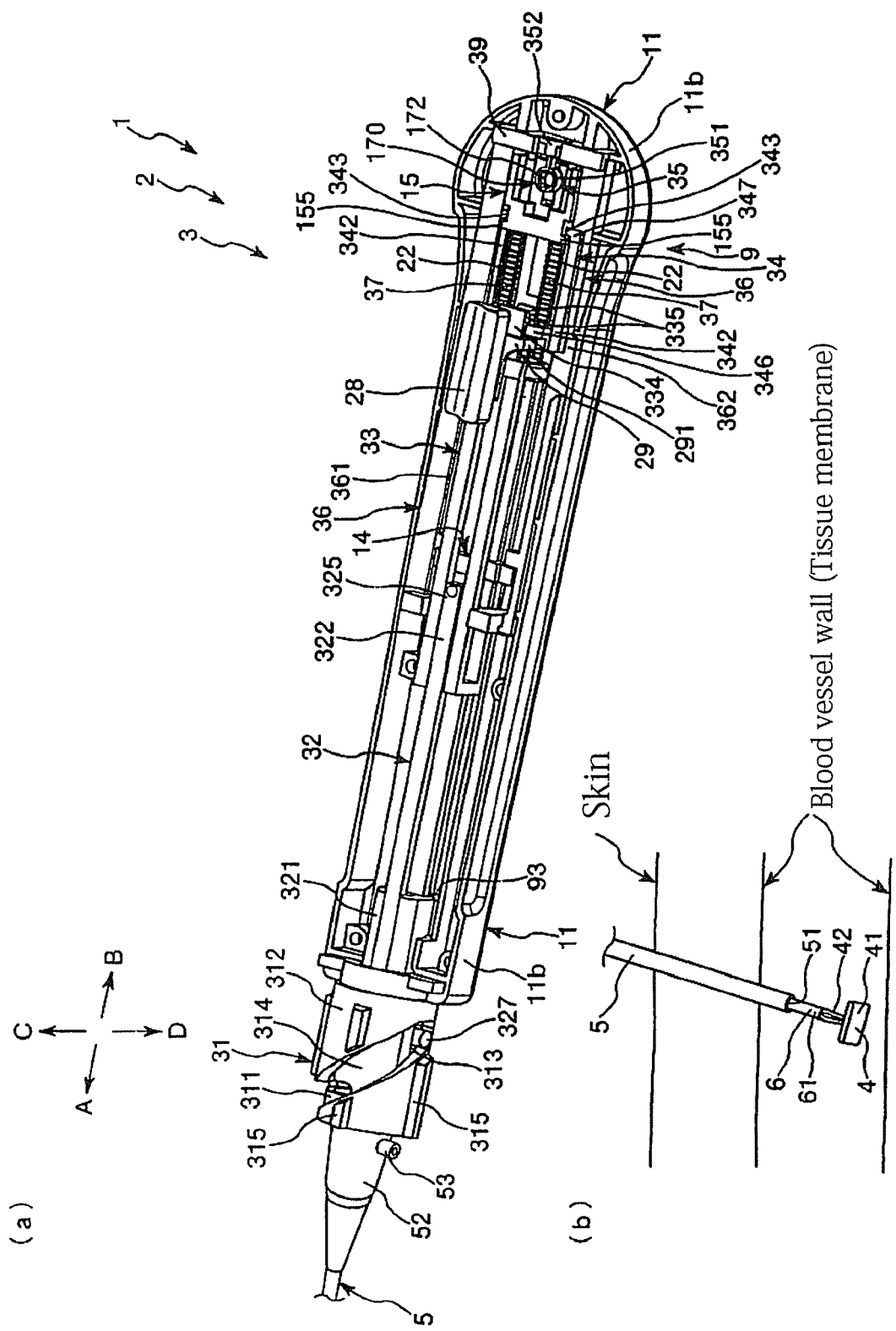
FIGS. 13(a) and 13(b) are perspective views illustrating other operational aspect of the tissue closing device shown in FIG. 1.
Figure 14:
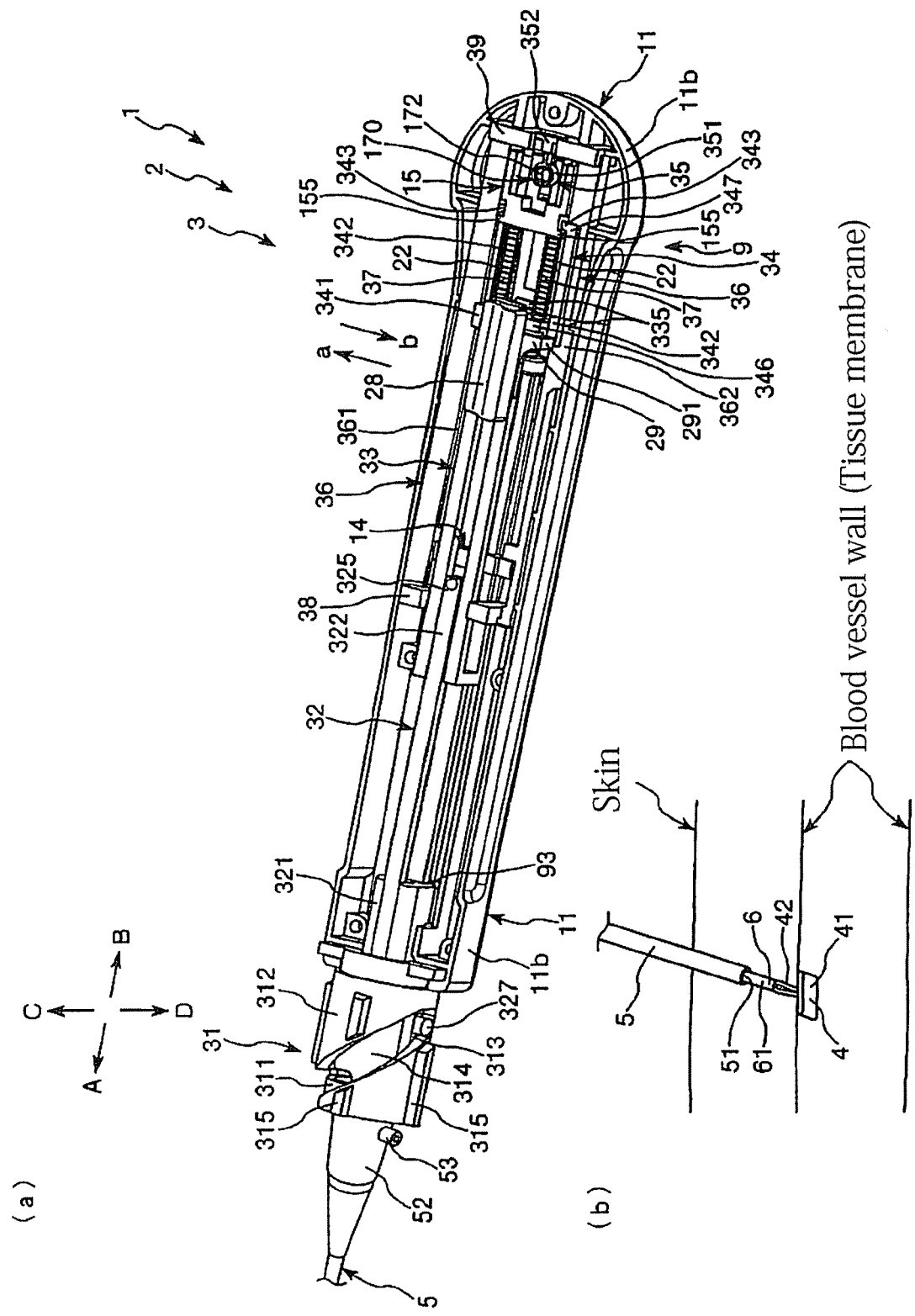
FIGS. 14(a) and 14(b) are perspective views illustrating additional operational aspect of the tissue closing device shown in FIG. 1.
Figure 15:
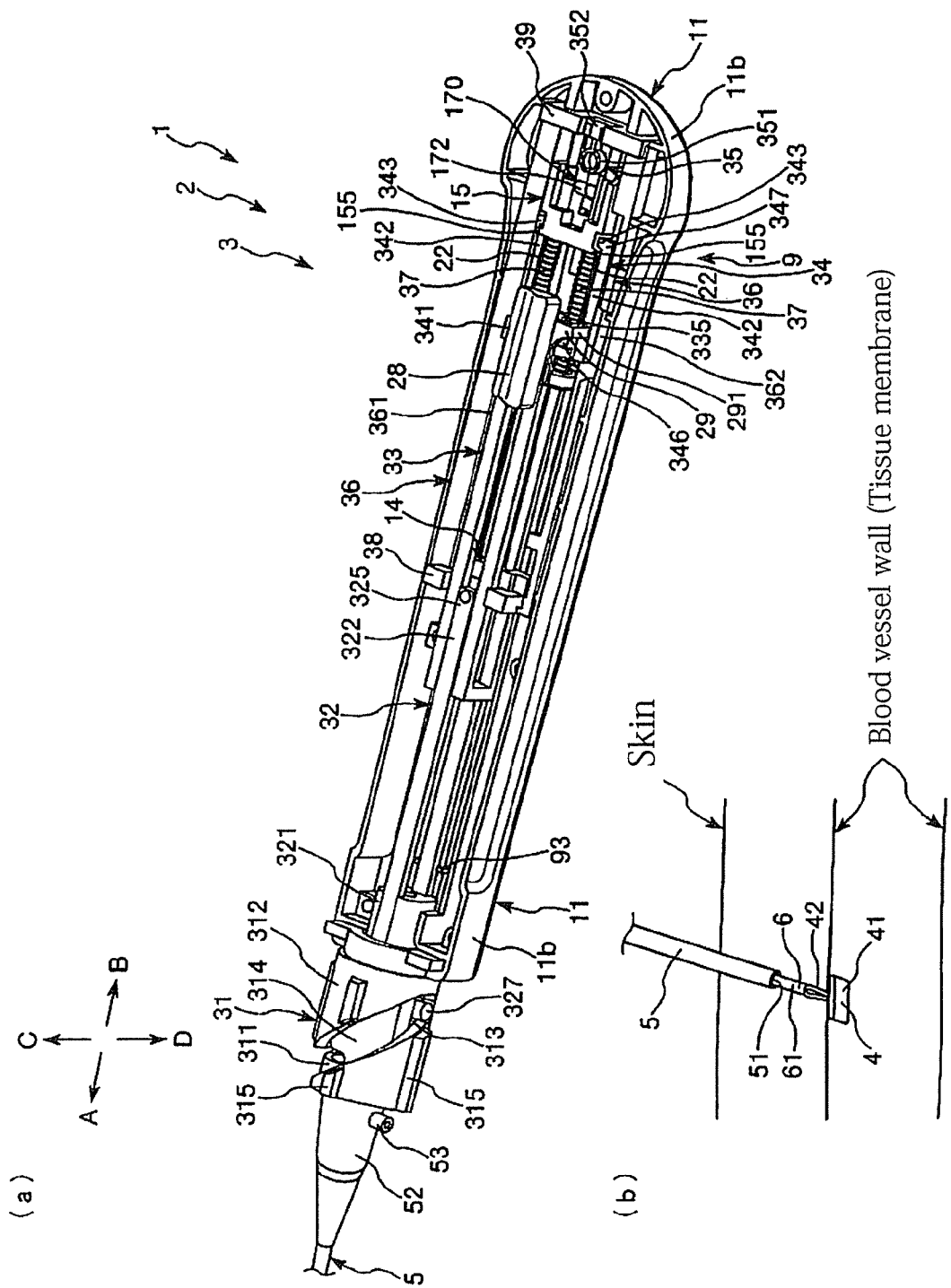
FIGS. 15(a) and 15(b) are perspective views showing other operational aspect of the tissue closing device shown in FIG. 1.
Figure 16:
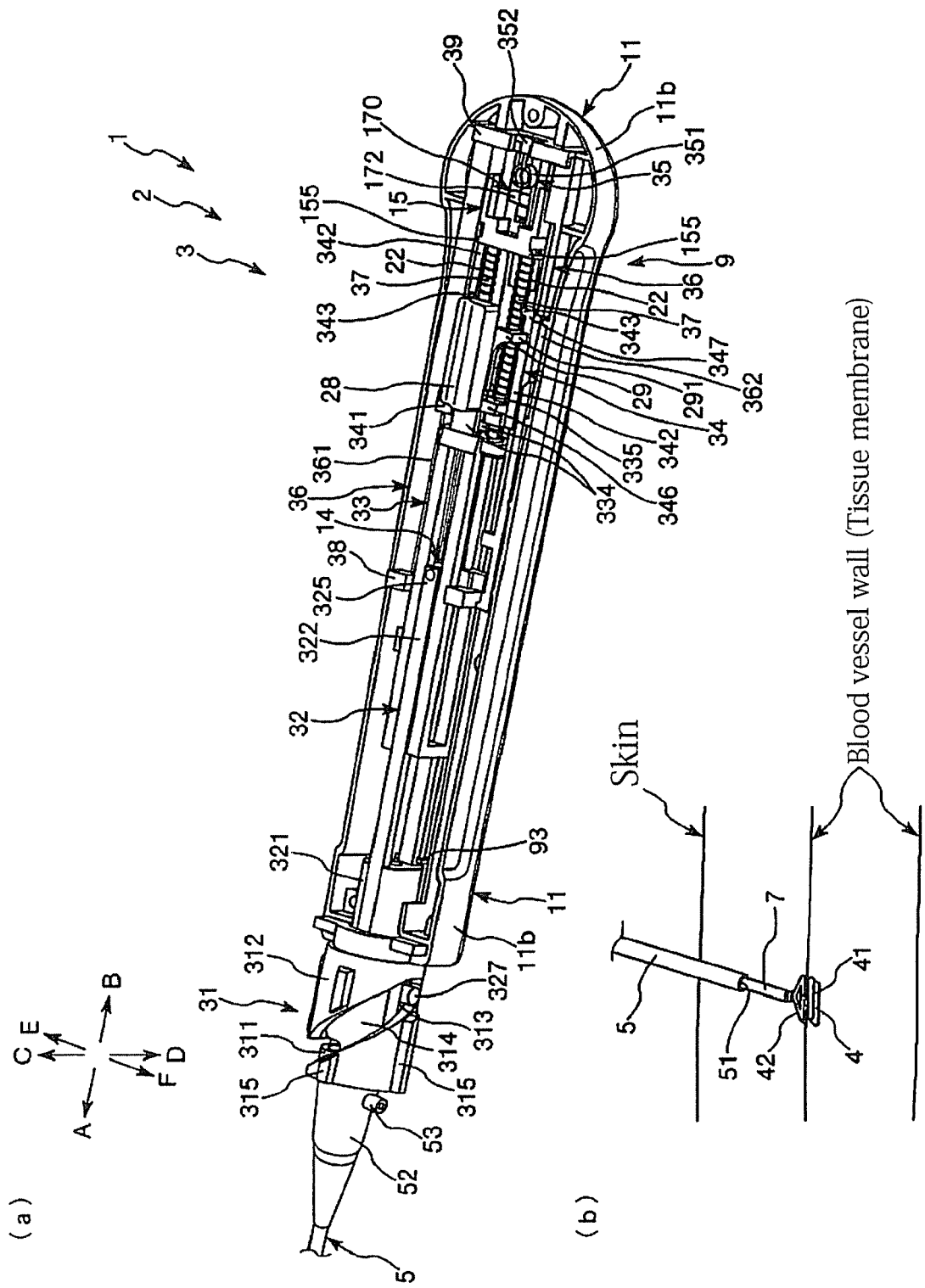
FIGS. 16(a) and 16(b) are perspective views illustrating further operational aspect of the tissue closing device shown in FIG. 1.
Figure 17:
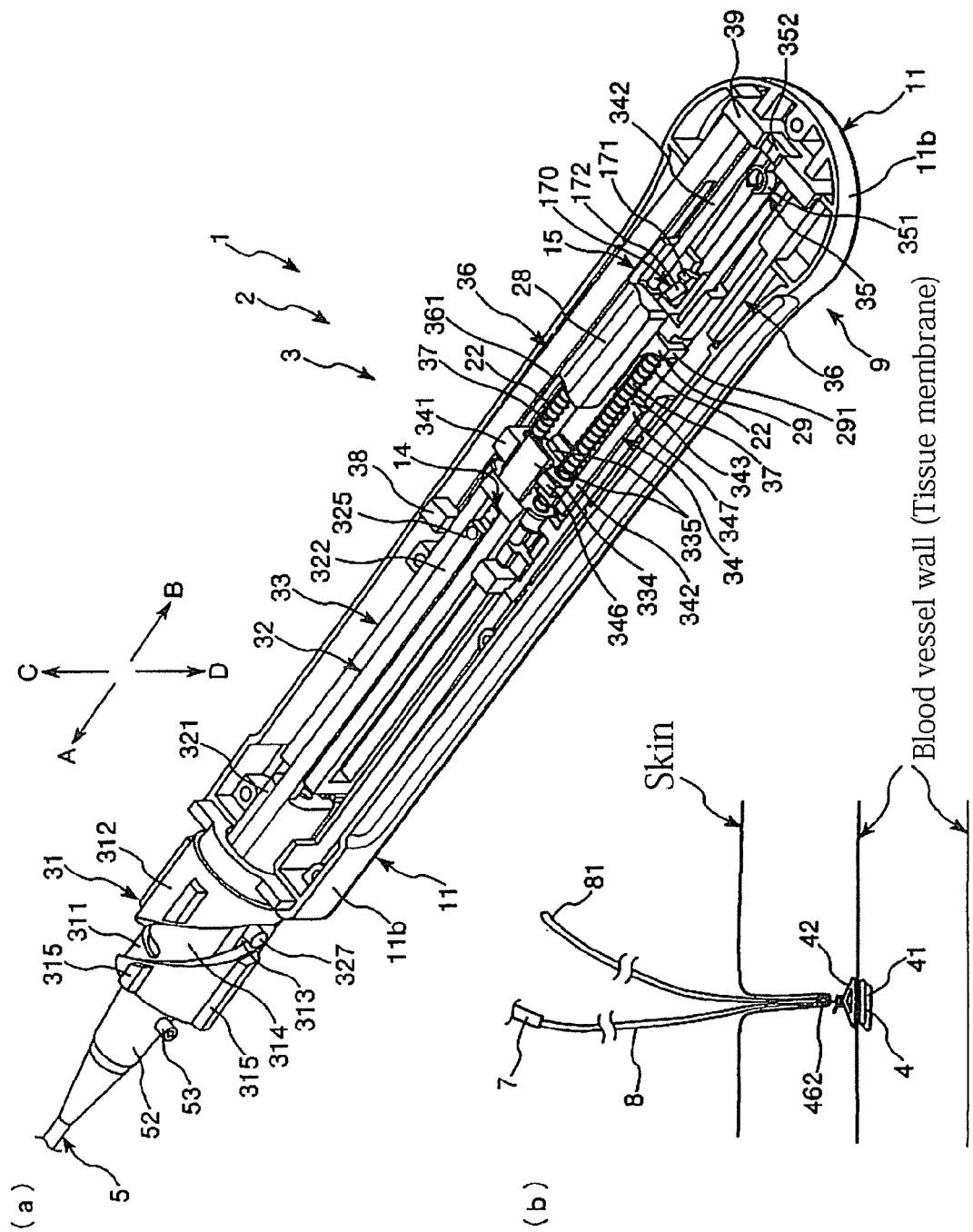
FIGS. 17(a) and 17(b) are perspective views illustrating other operational aspect of the tissue closing device shown in FIG. 1.
Figure 18:
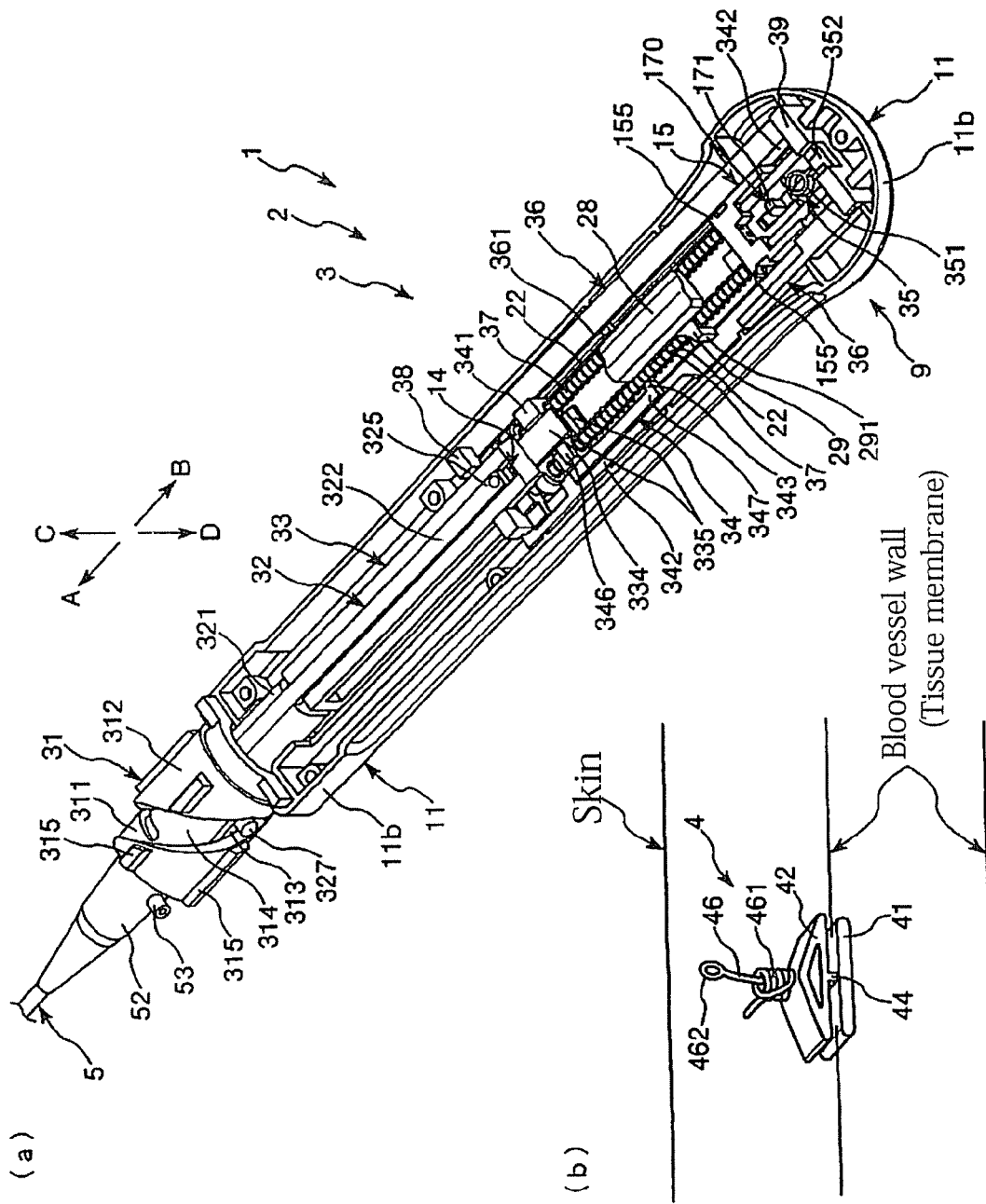
FIGS. 18(a) and 18(b) are perspective views showing other operational aspect of the tissue closing device shown in FIG. 1.

In this case, when the clip 4 is retained in the opening part 61 of the cover tube 6, the deformation part 42 of the clip 4 is in the form in which it is expanded in the direction substantially perpendicular to the seal part 41 (in the longitudinal direction (axial direction) of the cover tube 6) as shown in FIG. 11A and is contracted in a direction substantially parallel to the seal part 41 (in a radial direction of the cover tube 6). Then, as the knot 461 is gradually moved in the distal direction and the thread 46 is tightened as result, the corner portion 421 of the deformation part 42 is gradually moved toward the lower side in FIGS. 11A-11D, and the deformation part 42 is continuously deformed from the form shown in FIG. 11A through the form shown in FIG. 1$l$ B to the form shown in FIGS. 11C and 11D in which a tissue membrane can be sandwiched (clamped) between the seal part 41 and the deformation part 42 to close a wound hole. In other words, the deformation part 42 is gradually contracted in the direction substantially perpendicular to the plane of the seal part 41 (in the longitudinal direction of the cover tube 6) and gradually expanded in the direction parallel to the seal part 41 (in the radial direction of the cover tube 6).

In addition, as described above, the knot 461 is so formed as to be movable in the distal direction only when a strong force is exerted on the knot 461. Therefore, the condition where the deformation part 42 is in a predetermined form is maintained by the thread 46.

Thus, with the clip 4 disclosed here, the degree of deformation of the deformation part 42 can be continuously controlled (adjusted). That is, the distance between the two corner portions 421, 422 can be continuously controlled or adjusted. In other words, in the condition where the deformation part 42 is deformed into a predetermined form, the condition can be maintained. This makes it possible to address various cases (various states (situations) of tissue membrane such as blood vessel wall), such as a person with a thicker tissue membrane, a person with a thinner tissue membrane, a person with a harder tissue membrane, a person with a softer tissue membrane, etc.

The configuration of the clip (closure) is naturally not limited to the above-described configuration insofar as the clip (closure) has a seal part and a deformation part.

For instance, the shape of the deformation part of the clip is not limited to a tetragon but may be any of other polygons, or may be a cornerless frame-shape member such as a circular annular shape, an elliptic annular shape, etc.

In addition, the deformation part of the clip may be composed of a spongy porous material containing a biodegradable material (synthetic resin material), e.g., collagen, as a main material, an aggregate of fibers or the like.

Also, the fixing part for the clip is not limited to a filamentous element.

The retaining member 18 is now described.

Figure 8:
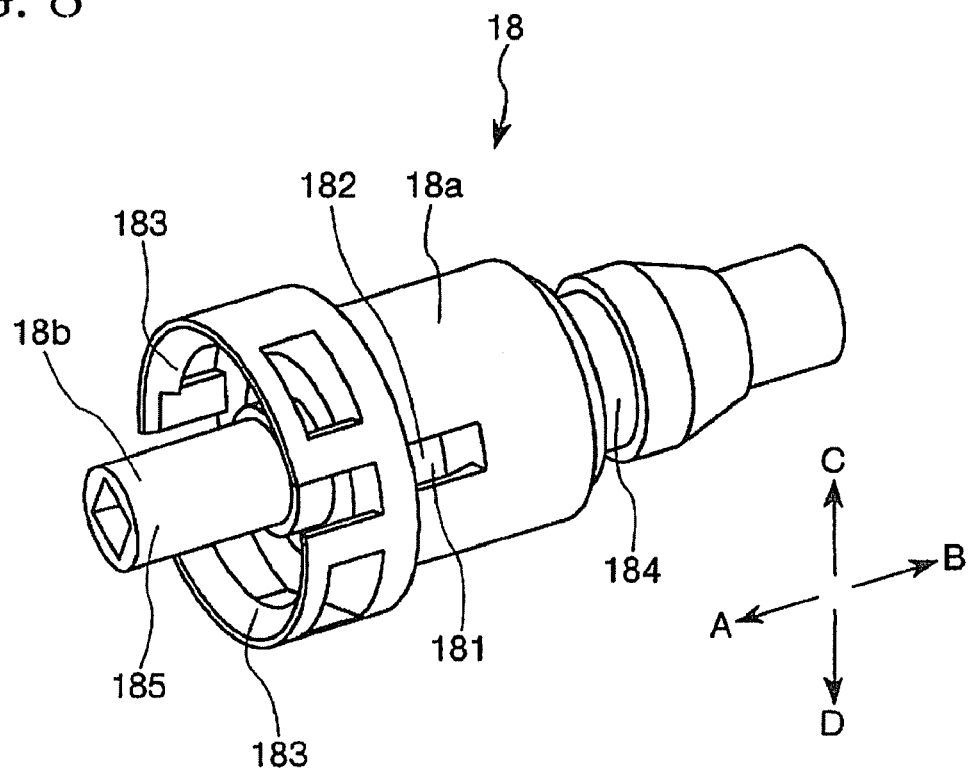
FIG. 8 is a perspective view of a retaining member of the tissue closing device shown in FIG. 1.
Figure 9:
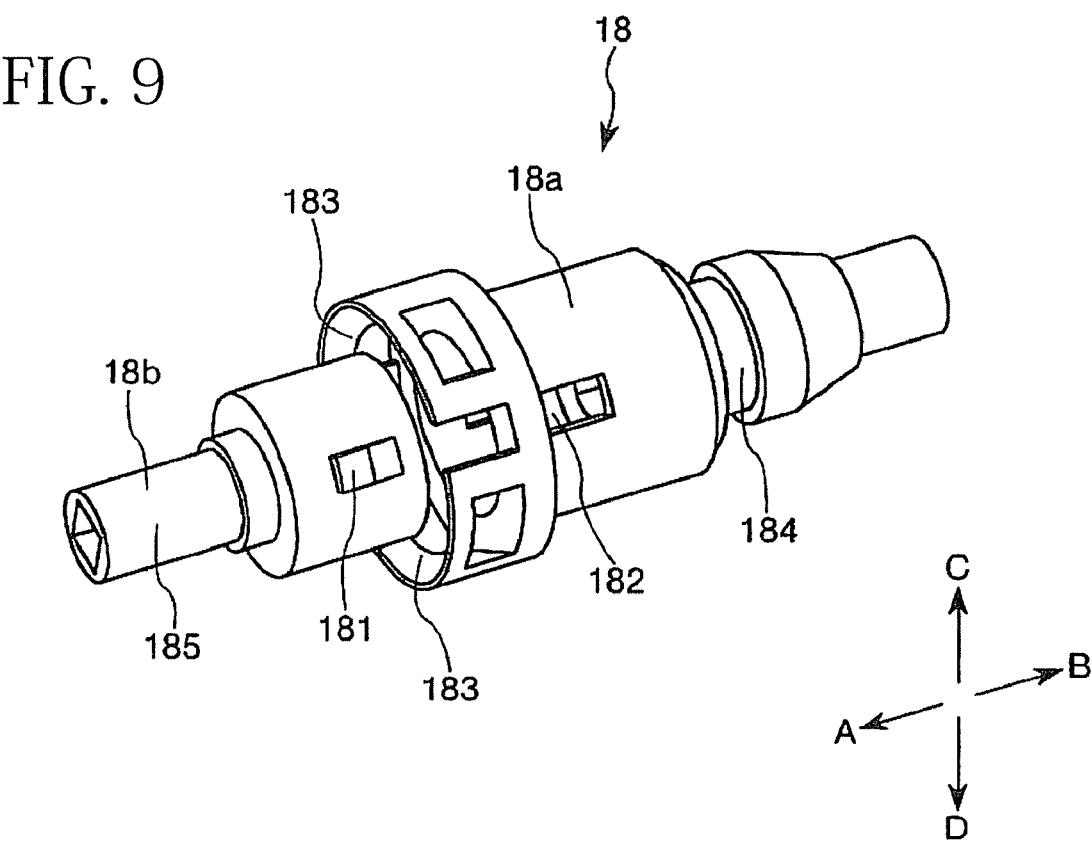
FIG. 9 is a perspective view of the proximal-side member and the distal-side member of the retaining member shown in FIG. 8.

As shown in FIGS. 8-10, the retaining member 18 is substantially tubular in overall shape, and is composed of a proximal-side member 18a disposed on the proximal side and a distal-side member 18b disposed on the distal side.

The proximal-side member 18a and the distal-side member 18b are integrated with each other, with the distal-side member 18b fitted in the inside (inner peripheral side) of the proximal-side member 18a. In addition, the distal-side member 18b is provided with a pair of projecting portions 181 at outer peripheral portions of the distal side member 18b. The proximal-side member 18a is provided with side holes 182 in portions corresponding to the projecting portions 181. As a result, when the distal-side member 18b is fitted into the proximal-side member 18a, the projecting portions 181 of the distal-side member 18b engaged edge portions fronting on the corresponding side holes 182 in the proximal-side member 18a, whereby the proximal-side member 18a and the distal-side member 18b are fixed to each other. FIGS. 8 and 10 illustrate the projecting portion 181 and the side hole 182 on only one side, it being understood that a similar projecting portion 181 and side hole 182 exist on the other side.

At an inner peripheral portion on the distal side of the retaining member 18, a pair of ribs (claws) 183 are formed. These claws 183 are adapted to be inserted into the groove 54 of the hub (connector) 52 of the sheath 5 to engage the surfaces inside the groove 54. The ribs 183 are each circumferentially extending ribs. By virtue of the ribs 183 and the groove 54, the retaining member 18 and the hub 52 of the sheath 5 are connected to each other and this condition is maintained. Therefore, the ribs 183 and the groove 54 constitute a first connecting part connecting the retaining member 18 and the hub 52 of the sheath 5.

A groove 184 is formed at an outer peripheral portion on the proximal side of the retaining member 18. The groove 184 receives the pair of claws 326 of the base portion 321 of the first charge member 32. The claws 326 are adapted to engage surfaces inside the groove 184. The groove 184 is formed along the circumferential direction over the circumference of the retaining member 18. By virtue of the groove 184 and the claws 326, the retaining member 18 and the proximal part 9 are connected to each other and this condition is maintained. Therefore, the groove 184 and the claws 326 constitute a second connecting part connecting the retaining member 18 and the proximal part 9.

The retaining member 18 has an accommodating part 190 which includes: a wide space part 191 possessing a comparatively wide space (lumen) (wide space); a narrow space part 192 provided on the distal side relative to the wide space part 191 and possessing a space (narrow space) narrower than the pace in the wide space part 191; and a transition part 193 provided between the wide space part 191 and the narrow space part 192 and provided therein with a space communicating the wide space and the narrow space. The relative wideness or largeness of the area in cross-section of the space (section perpendicular to the axis) is taken as the wideness or largeness of space.

The wide space part 191 is composed of a widest space portion 1911 having a widest space and provided on the distal side, and a proximal-side space portion 1912 provided on the proximal side relative to the widest space portion 1911.

In the initial condition (the condition immediately upon assembly), the clip 4 is contained (retained) in the accommodating part 190 (in this embodiment, the wide space part 191 and the transition part 193). In this case, the majority of the deformation part 42 of the clip 4 is contained or positioned in the proximal-side space portion 1912 of the wide space part 191, and the residual part or remainder of the deformation part 42 of the clip 4 is contained or positioned in the widest space portion 1911. The seal part 41 is contained in the transition part 193 and the widest space portion 1911 of the wide space part 191 (i.e., the seal part 41 spans between the transition part 193 and the widest space portion 1911).

The cross-sectional shape (space shape) of the proximal-side space portion 1912 is substantially tetragonal, with the vertexes being rounded. A predetermined pair of sides of the tetragon are oriented in a direction perpendicular to the sheet plane of FIG. 10, while the other pair of sides is oriented in the vertical direction in FIG. 10. This results in the clip 4 being contained in such a posture that the direction of the width W of the seal part 41 shown in FIG. 3 is in the direction perpendicular to the sheet plane of FIG. 10.

In the initial condition, in the configuration shown in the figures, a slight load may be exerted on the deformation part 42 from the proximal-side space portion 1912 to such an extent as not to produce any problem. In this case, the deformation part 42 is contained in the condition where a load for compressing the deformation part 42 in a radial direction (in a direction perpendicular to the longitudinal direction) of the cover tube 6 is slightly exerted on the deformation part 42 (in the condition where the deformation part 42 is slightly folded so as to expand in the longitudinal direction of the cover tube 6), as compared to the natural condition in which no external force is exerted.

In assembling the tissue closing device 1, the clip 4 is contained at a predetermined position in an inner space of the proximal-side member 18a, and thereafter the proximal-side member 18a and the distal-side member 18b are integrated with each other by fitting. This helps ensure that the clip 4 can be contained into the accommodating part 190 without exerting any load of a trouble-making magnitude on the deformation part 42 of the clip 4.

The clip 4 may be contained in such a manner that no load is exerted on the deformation part 42 and, hence, the deformation part 42 is not deformed at all. In addition, the clip 4 may be contained in only the wide space part 191.

In the initial condition, the cover tube 6 and the fixing tube 7 are inserted into (positioned in) the lumen of the retaining member 18 via the proximal end of the retaining member 18. In this case, the opening part 61 of the cover tube 6 is located in the wide space part 191, while the distal portion 71 of the fixing tube 7 is located in a portion, on the proximal side relative to the wide space part 191, of the retaining member 18. Since the fixing tube 7 which is comparatively hard is located in the lumen of the retaining member 18, the cover tube 6 can be inhibited or prevented from kinking.

In addition, the cross-sectional shape (the lumen shape) of the inside of the retaining member 18 at a portion (proximal portion 186) on the proximal side relative to the wide space part 191 is substantially elliptic. On the other hand, the cross-sectional shape of the distal portion 71 of the fixing tube 7 and the cross-sectional shape of the cover tube 6 at a portion corresponding to the distal portion 71 of the fixing tube 7 are substantially elliptic, respectively, as mentioned above. Therefore, the cover tube 6 and the fixing tube 7 can be inhibited or prevented from rotating relative to the retaining member 18. The orientation of the ellipses is set so that the deformation part 42 of the clip 4 is inserted into the opening part 61 of the cover tube 6 when the retaining member 18 is moved toward the proximal side.

The cross-sectional size of the opening part 61 of the cover tube 6 is larger than the lumen of the proximal portion 186 of the retaining member 18. This helps ensure that the retaining member 18 is inhibited or prevented from coming off the distal portion of the cover tube 6.

In addition, the inner diameter of a most proximal portion 187 of the retaining member 18 gradually increases along the direction from the distal side toward the proximal side. The surface of that gradually increasing diameter portion is rounded as shown in FIG. 10. This helps inhibit or prevent the cover tube 6 from buckling when the retaining member 18 is moved toward the proximal side.

The inner diameter of a boundary portion between the proximal portion 186 and the most proximal portion 187 of the retaining member 18 is preferably set so that blood will not leak via the gap between the retaining member 18 and the cover tube 6 or so that the leakage amount is very small. Specifically, the inner diameter of the boundary portion between the proximal portion 186 and the most proximal portion 187 of the retaining member 18 is preferably set to be slightly smaller than the outer diameter of the cover tube 6.

The retaining member 18 is configured so that the clip 4 passes through the transition part 193 into the narrow space part 192 when the retaining member 18 is moved toward the proximal side.

The transition part 193 has an inclined surface 194 on the lower side in FIG. 10. The inclined surface 194 is so inclined that its position is lower (in FIG. 10) on the proximal side than on the distal side (the inclined surface 194 slopes down from the distal side toward the proximal side).

When the retaining member 18 is moved toward the proximal side, the clip 4 is gradually folded along the inclined surface 194. Specifically, the seal part 41 of the clip 4 is gradually inclined or folded, relative to the deformation part, as it moves along the inclined surface 194.

On the other hand, the surface of the transition part 193 which is on the upper side in FIG. 10 (positioned opposite the surface 194) is not inclined. This helps contribute to smooth folding of the clip 4.

In addition, when the clip 4 is inserted into the narrowed space part 192, the load (the load in a radial direction of the cover tube 6) exerted on the deformation part 42 increases, and the deformation part 42 is compressed (compressed in the radial direction of the cover tube 6) as compared to its state in the initial condition. As a result, the deformation part 42 is brought into a form (see FIG. 11A) in which it is expanded in the direction (the longitudinal direction of the cover tube 6) substantially perpendicular to the seal part 41 of the clip 4 in the basic form shown in FIG. 3 and is contracted in the direction (the radial direction of the cover tube 6) substantially parallel to that seal part 41. Simultaneously, the seal part 41 is inclined (folded) more. Consequently, the clip 4 is folded completely and, in this folded condition (the condition where the deformation part 42 is compressed), the deformation part 42 is pushed into and retained in the opening part 61 of the cover tube 6 (with respect to the opening part 61 and the deformation part 42 as shown in FIG. 13B).

The retaining member 18 has a tubular portion 185 possessing a lumen which communicates with the space in the narrowed space part 192. The tubular portion 185 is formed at a central portion of a distal portion of the retaining member 18 and projects toward the distal side. In connecting the hub 52 of the sheath 5 and the retaining member 18 to each other, the tubular portion 185 is inserted into the hub 52 through the hemostatic valve of the hub 52, resulting in the space in the narrow space part 192 and the through-hole 51 in the sheath 5 communicating with each other through the lumen of the tubular portion 185.

The cross-sectional shape (the lumen shape) of the portion of the tubular part 185, on the distal side relative to the narrow space part 192, is substantially tetragonal. The tetragonal shape is so set that when the retaining member 18 is moved toward the proximal side, the seal part 41 (the direction of the width W shown in FIG. 3) of the clip 4 coincides substantially with one of the diagonals of the tetragon. This helps ensure that the seal part 41 is inhibited or prevented from rotating when the clip 4 is passed through the lumen of the tubular portion 185.

In addition, the tubular portion 185 is so configured that the resistance (frictional resistance) at the time of passage of the clip 4 through the lumen of the tubular portion 185 is greater than the resistance at the time of passage of the clip 4 through the narrow space part 192. Specifically, the tubular portion 185 (the distal-side member 18*b*) is so configured that the length of the diagonal of the tetragonal shape thereof is smaller than the width W of the seal part 41, and the tubular portion 185 is flexible and deformable. As a result, when the seal part 41 passes through the lumen of the tubular portion 185, an appropriate degree of resistance (frictional resistance) is developed, whereby the deformation part 42 of the clip 4 is assuredly pushed into the opening part 61 of the cover tube 6, where it is retained. Besides, since the resistance is an appropriate degree of resistance, it does not hamper the passage of the seal part 41 through the lumen of the tubular portion 185.

When the retaining member 18 is moved toward the proximal side, the clip 4 with its deformation part 42 retained in the opening part 61 of the cover tube 6 is passed through the lumen of the tubular portion 185, is discharged from the retaining member 18, and is inserted into the through-hole 51 in the sheath 5. In this case, the clip 4 is inserted into the through-hole 51 of the sheath 5 without making contact with the hemostatic valve of the hub 52. Therefore, the clip 4 is assuredly inserted into the through-hole 51 of the sheath 5 while being in a normal state. In this manner, transition is made from the condition where the clip 4 is contained in the accommodating part 190 of the retaining member 18 to the condition where the deformation part 42 of the clip 4 is retained in the opening part 61 of the cover tube 6.

The material constituting the retaining member 18 is not limited to any particular materials. For example, a resin, a metal or the like can be used as the material forming the retaining member 18. in order to secure visibility of the inside of the retaining member 18, the material is preferably a light-transmitting (substantially transparent or translucent) material. Further, the tubular portion 185 is preferably formed of a comparatively flexible resin material or the like so that it can be deformed.

The staunching procedure involving use of the tissue closing device 1 disclosed here, and the action or operation of the tissue closing device, is now described.

As shown in FIG. 12B, a sheath 5 is left indwelling after a treatment of therapy (PCI) or diagnosis (CAG) conducted using a catheter. This sheath 5 is used during implementation of the tissue closing device here. A distal portion of the sheath 5 is in a state in which it passes through a wound hole and is inserted in a blood vessel.

FIGS. 1 and 2 illustrate the initial condition of the tissue closing device in which the lever 28 is located at the locking position, the projected portion 291 of the lock part 29 is in contact with the distal side of the projection 346 of the slide coupling member 34, and the projection 346 is locked by the projected portion 291, whereby the slide coupling member 34 is inhibited from moving in the distal direction.

First, the operator (user) connects the retaining member 18 of the arrangement device 3 to the hub 52 of the sheath 5. To do this, the tubular portion 185 of the retaining member 18 is inserted into the hub 52 through the hemostatic valve of the hub 52, and the hub 52 is pushed into the inside of a distal portion of the retaining member 18. As a result, the ribs 183 of the retaining member 18 are positioned in the groove 54 of the hub 52, and are engaged with the surfaces inside the groove 54. Consequently, the retaining member 18 and the hub 52 of the sheath 5 are connected with each other, and this condition is maintained. Before the retaining member 18 is connected to the hub 52 of the sheath 5, the clip 4 is positioned in the retaining member 18. That is, the clip 4 is generally positioned as shown in the solid-line position of FIG. 10.

Next, the sheath 5 and the retaining member 18 are moved toward the proximal side relative to the cover tube 6. The distal end of the sheath 5 remains in the wound hole.

As a result, the clip 4 is abutted on the distal end of the opening part 61 of the cover tube 6 and is locked (pressed to the distal side) by the opening part 61. By this operation, the seal part 41 of the clip 4 is gradually inclined along the inclined surface 194 as illustrated in FIG. 10.

Then, when the clip 4 is inserted into the narrowed space part 192, the load exerted on the deformation part 42 in a radial direction of the cover tube 6 is increased, so that the deformation part 42 is compressed in the radial direction of the cover tube 6 as compared with its shape in the initial condition. The clip 4 is thus brought into a form in which it is expanded in the direction substantially perpendicular to the seal part 41 of the clip 4 in the basic form shown in FIG. 3 and is contracted in the direction substantially parallel to that seal part 41. Consequently, the clip 4 is folded (e.g., folded completely).

In addition, when the seal part 41 is passed through the lumen of the tubular portion 185, an appropriate extent of resistance is developed, whereby the deformation part 42 of the clip 4 is pushed into the opening part 61 of the cover tube 6 to be retained there.

Then, the clip 4 with its deformation part 42 retained in the opening part 61 of the cover tube 6 is passed through the lumen of the tubular portion 185, is discharged from the retaining member 18, and is inserted into the through-hole 51 in the sheath 5. In this manner, transition is made from the condition where the clip 4 is contained in the accommodating part 190 of the retaining member 18 to the condition where the deformation part 42 of the clip 4 is retained in the opening part 61 of the cover tube 6.

Further, the sheath 5 and the retaining member 18 are moved toward the proximal side relative to the cover tube 6, and the retaining member 18 is connected to the base portion 321 of the first charge member 32. In this case, a proximal portion of the retaining member 18 is pushed into the inside of the base portion 321. The claws 326 of the base portion 321 are inserted into the groove 184 of the retaining member 18, and are engaged with the surfaces inside the groove 184. As a result, the base portion 321 and the retaining member 18 (the proximal part 9) are connected with each other, and this condition is maintained. In other words, the base portion 321 and the hub 52 are connected to each other through the retaining member 18 (the base portion 321 and the retaining member 18 and the hub 52 are integrated).

Subsequently, as shown in FIGS. 12A and 12B, in the condition where the position of the distal portion of the slot 313 in the inner tube part 311 of the connector 31 and the position of the distal portion of the slot 314 in the outer tube part 312 coincide with each other, the sheath 5 and the retaining member 18 and the first charge member 32 are pushed (moved) in the proximal direction, whereby the base portion 321 of the first charge member 32 is inserted into the inner tube part 311, and the projection 327 of the base portion 321 is located at the position of the distal portion of the slot 313 in the inner tube part 311 and the distal portion of the slot 314 in the outer tube part 312.

In this case, the second charge member 33 is moved in the proximal direction together with the first charge member 32, whereby the coil springs 22 are gradually contracted (deformed, or activated, or charged) between the second charge member 33 and the thread support part 15. Then, the pair of claws 335 of the second charge member 33 engaged the base portion 341 of the slide coupling member 34. Thereafter, the proximal portions 325 of the pair of rod-like elements 322 of the first charge member 32 are inserted into the pair of grooves 91 in the casing 11 (see FIG. 2), and the interval between the proximal portions 325 of both the rod-like elements 322 is enlarged (see FIG. 2), whereby the pair of recesses 336 in the distal portion of the second charge member 33 and the pair of projected portions 323 of the first charge member 32 are disengaged from each other (see FIG. 2).

As a result, the second charge member 33 is made unmovable relative to the slide coupling member 34 and the thread support part 15, and the coil springs 22 are maintained in the contracted state (deformed state, or active state). In addition, the fixing tube 7 is retained (substantially fixed) by the second charge member 33 and the slide coupling member 34 (the thread support part 15 is inhibited from moving relative to the fixing tube 7 in the proximal direction). In other words, the positional relations among the second charge member 33, the slide coupling member 34, the thread support part 15, the fixing tube 7 and the coil springs 22 are fixed, so that these components subsequently move together as one body or a single unit. This condition is referred to as the charged condition.

In this condition, the clip 4 (the seal part 41 of the clip 4) is contained in the through-hole (lumen) 51 of the sheath 5. Therefore, the clip 4 would not damage the blood vessel wall at the time of inserting the base portion 321 of the first charge member 32 into the inner tube part 311. Thus, relatively high safety is secured.

Next, as shown in FIGS. 13A and 13B, the outer tube part 312 is rotated in a predetermined direction (in the example shown, counterclockwise as viewed from the distal direction). This results in the projection 327 being pushed in the proximal direction by an edge portion, fronting on the slot 314, of the outer tube part 312, and is gradually moved in the proximal direction along the slot 313 in the inner tube part 311, and the seal part 41 of the clip 4 and the cover tube 6 are gradually projected from the distal portion of the sheath 5. In this manner, the opening part 61 of the cover tube 6 projects from the distal portion of the sheath 5, and the seal part 41 of the clip 4 projects for insertion into the blood vessel. In addition, the base portion 321 of the first charge member 32 is moved in the proximal direction and inserted further into the inner tube part 311 to be fixed there. The first charge member 32 is inhibited from moving in the proximal direction beyond the pair of projections 93 of the casing 11, since the base portion 321 of the first charge member 32 abuts on the projections 93. Since the first charge member 32 and the second charge member 33 have already been disengaged from each other, the second charge member 33 is not moved.

Thus, in the condition where the projection 327 at the base portion 321 of the first charge member 32 is located at the position of the distal portion of the slot 313 in the inner tube part 311 and the distal portion of the slot 314 in the outer tube part 312, the clip 4 is contained in the through-hole 51 of the sheath 5. With the outer tube part 312 rotated from this condition, the base portion 321 of the first charge member 32 gradually moves in the proximal direction so that the seal part 41 of the clip 4 can be securely prevented from abruptly projecting from the distal end of the sheath 5 toward the blood vessel wall.

Subsequently, the casing 11 of the proximal part 9 is gripped by the fingers of the user's hand, and the proximal part 9, i.e., the body part 2 (arrangement device 3) is slowly moved in one direction, i.e., in the direction for pulling out of the wound hole (in the proximal direction). As shown in FIG. 14B, this causes the wound hole and the peripheral portion of the wound hole to be covered with the seal part 41 of the clip 4 from the inside of the blood vessel wall. The positioning of the seal part 41 is this performed. During this operation, the deformation part 42 of the clip 4 is moved to the outside of the blood vessel.

When the resistance upon contact of the seal part 41 with the wound hole and the surrounding tissues (surface contact resistance) is sensed during the movement of the body part 2 in the direction for pulling the device out of the wound hole while covering the wound hole and the peripheral portion of the wound hole with the seal part 41, the operator judges that the contact of the seal part 41 with the wound hole and the surrounding tissues (surface contact) has occurred and the positioning of the seal part 41 has been completed.

In this case, the members for connecting the clip 4, the thread support part 15 and the casing 11 along the longitudinal direction of the arrangement device 3 do not include any member that expands and contracts in the longitudinal direction of the arrangement device 3, such as a spring, and the distance between the clip 4 and the casing 11 is kept constant (inclusive of substantially constant). Therefore, the operator can directly sense the force exerted on the seal part 41 of the clip 4 by a finger of a hand so that the operator can accurately sense the resistance upon contact of the seal part 41 of the clip 4 with the wound hole and the surrounding tissues.

In addition, movement of the second charge member 33, the slide coupling member 34, the thread support part 15, the fixing tube 7 and the coil springs 22 in the distal direction is inhibited by the lock part 29. Therefore, it is possible to relatively securely prevent the coil springs 22 from being actuated before the positioning of the seal part 41 is completed.

Consequently, the positioning of the seal part 41 of the clip 4 can be carried out quite easily and assuredly.

Next, as shown in FIGS. 14A and 14B, the lever 28 is moved in the direction of the arrow b, and is located in the unlocking position. This results in movement of the lock part 29 in the direction of arrow b, and the projected portion 291 of the lock part is moved (retracted) sideways relative to the projection 346 of the slide coupling member 34 (to a position where the projection 346 is absent). The projection 346 is thus unlocked from the projected portion 291. Consequently, movement of the second charge member 33, the slide coupling member 34, the thread support part 15, the fixing tube 7 and the coil springs 22 in the distal direction is permitted on condition that the condition where movement of the thread support part 15 is inhibited by the stopper 35 is canceled.

Subsequently, the body part 2 (the arrangement device 3) is slowly moved in the direction for pulling out of the wound hole (in the proximal direction), whereby the body part 2 is pulled out of the wound hole. Accordingly, all the steps (operations) are carried out sequentially and continuously to close the wound hole with the clip 4, and the clip 4 is arranged (left to indwell) in the living body. This is described below in more detail.

First, when the proximal part 9 (the casing 11) is moved in the proximal direction, as shown in FIGS. 15A and 15B, the thread part 15 is pulled in the distal direction through the thread 8, since the seal part 41 of the clip 4 is in contact with the inner surface (the surface which is distal from the body surface) of the blood vessel wall. Then, when the force (pulling force) exerted on the thread support part 15 through the thread 8 exceeds a predetermined threshold, the projection 172 of the pin 170 is released from the gap in the stopper body 351 of the stopper 35, and the second charge member 33, the slide coupling member 34, the thread support part 15, the fixing tube 7 and the coil springs 22 move together as a single body or unit in the distal direction relative to the casing 1.

Here, in the positioning of the seal part 41 in the condition where movement of the slide coupling member 34 in the distal direction is inhibited by the lock part 29, even if the positioning is incomplete due, for example, to the clip 4 being caught in the blood vessel, the clip 4 can be expected to be released before the pin 170 is released (unlocked) from the stopper 35, and the clip 4 can be moved to the wound hole to thereby bring the seal part 41 into contact with the wound hole and the surrounding tissues. Thus, the positioning of the seal part 41 of the clip 4 is conducted in such a way that the seal part 41 can be relatively assuredly brought into contact with the wound hole and the surrounding tissues.

When the second charge member 33, the slide coupling member 34, the thread support part 15, the fixing tube 7 and the coil springs 22 are moved in the distal direction relative to the casing 11, the deformation part 42 of the clip 4 is moved in the distal direction relative to the cover tube 6 together with the fixing tube 7, and the deformation part 42 is distally released from the distal portion of the cover tube 6, resulting in the deformation part 42 being deformable.

Then, when the proximal portions 347 of the pair of rod-like elements 342 of the slide coupling member 34 are moved until located at the hole portions 362 of the pair of rails 36, as shown in FIGS. 16A and 16B, the proximal portions 347 of the rod-like elements 342 become movable (displaceable) sideways (in the directions of arrows E and F), respectively. On the other hand, the slide coupling member 34 is biased in the distal direction relative to the thread support part 15 by the restoring forces of the coil springs 22. By virtue of these biasing forces, the proximal portions 347 of the rod-like elements 342 are moved substantially sideways along the projections 155, to be inserted (retracted) into the hole portions or cutouts 362, and the claws 343 of the rod-like elements 342 are disengaged from the projections 155 of the thread support part 15.

As a result, the coupling between the thread support part 15 and the second charge member 33 by the slide coupling member 34 is canceled, and the thread support part 15 becomes movable in the proximal direction relative to the second charge member 33, the slide coupling member 34 and the fixing tube 7. In addition, by canceling the coupling between the thread support part 15 and the second charge member 33 through the slide coupling member 34, movement of the thread support part 15 relative to the second charge member 33, the slide coupling member 34 and the fixing tube 7 or vice versa is permitted, whereby the restraint for retaining the coil springs 22 in the deformed state (active state) is canceled.

Consequently, the thread support part 15 is moved in the proximal direction relative to the second charge member 33, the slide coupling member 34 and the fixing tube 7 by the restoring forces of the coil springs 22. Thus, the slide coupling member 34, the pair of projections 155 of the thread support part 15, the pair of projected portions 334 of the second charge member 33, and the hole portions 362 in the pair of rails 36 function as trigger means for actuating the coil springs 22 by canceling the restraint for retaining the coil springs 22 in the active (compressed) state. The slide coupling member 34, the pair of projections 155 of the thread support part 15, and the pair of projected portions 334 of the second charge member 33 function as restraining means for retaining the coil springs 22 in the active state. In addition, the operation (triggering operation) by which the proximal portions 347 of the rod-like elements 342 of the slide coupling member 34 coupling the thread support part 15 and the second charge member 33 to each other are moved sideways (in the direction for disengaging the claws 343 of the rod-like elements 342 from the projections 155 of the thread support part 15) is performed automatically by both the operator's operation of pulling off (moving) the proximal part 9 toward the proximal side and the biasing forces of the coil springs 22.

When the thread support part 15 is moved in the proximal direction relative to the fixing tube 7, the thread 8 is moved in the proximal direction, as shown in FIG. 16B. In this case, the thread 46 of the clip 4 is pulled in the proximal direction by the thread 8, and the knot 461 of the thread 46 of the clip 4 is locked by the distal portion 71 of the fixing tube 7. Further, the deformation part 42 is locked through the knot 461 (locked indirectly), whereby the knot 461 is moved in the distal direction, the thread 46 is tightened, and the deformation part 42 is deformed.

As a result, the deformation part 42 covers the wound hole and the peripheral portion of the wound hole from the outside of the blood vessel wall, while the seal part 41 covers the wound hole and the peripheral portion of the wound hole from the inside of the blood vessel wall. The blood vessel wall is sandwiched (clamped) between the seal part 41 and the deformation part 42 to close the wound hole. Then, the condition in which the deformation part 42 is in the above-mentioned form is maintained (fixed) by the thread 46.

When the proximal part 9 (the casing 11) is further moved in the proximal direction in the condition where the seal part 41 of the clip 4 is in contact with the inner surface of the blood vessel wall as shown in FIGS. 17A and 17B after the coupling between the thread support part 15 and the second charge member 33 by the slide coupling member 34 is canceled (the restraint for retaining the coil springs 22 in the deformed state is canceled), i.e., after the deformation of the deformation part 42 of the clip 4 is completed, the casing 11 is further moved in the proximal direction relative to the thread support part 15. In other words, the thread support part 15 is further moved in the distal direction relative to the casing 11.

Then, when the pin 170 provided in the thread support part 15 is moved until it is located on the distal side relative to the distal portion of the rib 92 of the casing 11, the pin 170 is turned at the stepped portion 921, and the projection 172 of the pin 170 is leveled (i.e., moved from an upright vertical position to a horizontal position).

As a result, the coupling between the thread 8 and the thread support part 15 through the pin 170 is canceled, whereby the coupling between the thread 8 and the thread 46 of the clip 4 is canceled (the retained state of the clip 4 retained by the thread 8 is canceled). Specifically, the fold-back portion 81 of the thread 8 is disengaged from the projection 172 of the pin 170, resulting in the thread 8 being able to be pulled out of the loop 462 of the thread 46 of the clip 4. Accordingly, the stepped portion 921 constitutes an uncoupling means for uncoupling the thread 8 and the thread 46 of the clip 4, and a retained state canceling means for canceling the retained state of the clip 4 by the thread 8.

Then, when the proximal part 9 (the casing 11) is moved in the proximal direction continually, only the body part 2 (ranging from the sheath 5 through the cover tube 6 to the distal portion of the fixing tube 7) is first pulled out of the patient's body. At this stage, as shown in FIG. 17B, the fold-back portion 81 of the thread 8 is located in the exterior of the patient's body in the state of being not yet released from the loop 462 of the thread 46 of the clip 4, and the clip 4 is being retained by the thread 8.

Specifically, in this tissue closing device 1, on a structure and mechanism basis, the length of the thread 8 is set to be comparatively large. Therefore, at the stage immediately after the body part 2 is pulled out of the patient's body, the fold-back portion 81 of the thread 8 is not yet released from the loop 462 of the thread 46 of the clip 4, and the clip 4 is retained by the thread 8. In addition, the fold-back portion 81 of the thread 8 is located outside the patient's body. Therefore, when the operator is gripping the body part 2 and the fold-back portion 81 of the thread 8, the clip 4 can be kept retained (secured) through the thread 8, which makes it possible to cope with various situations. Thus, a relatively very high safety is secured. In this case, for example, the operator can take out the clip 4 from the inside of the blood vessel by surgery while retaining the clip 4 through the thread 8.

If there is no problem, as shown in FIGS. 18A and 18B, the proximal part 9 (the casing 11) is moved further in the proximal direction, to pull off the thread 8 from the patient's body. Consequently, the clip 4 is disposed (left indwelling) in the living body.

As described above, the tissue closing device 1 disclosed here by way of an illustrated example, is configured so that in the initial condition, the deformation part 42 of the clip 4 is not retained in the opening part 61 of the cover tube 6 of the arrangement device 3. Therefore, the exertion of a load on the deformation part 42 can be prevented or restrained during the period until use of the tissue closing device 1 (e.g., during storage or the like). This makes it possible to prevent the deformation part 42 (the clip 4) from acquiring a semi-permanently set shape, and to prevent the deformation part 42 (the clip 4) from being deteriorated or broken.

At the time of use of the tissue closing device 1, the retaining member 18 is moved toward the proximal side, whereby the deformation part 42 of the clip 4 can be relatively easily and speedily retained in the opening part 61 of the cover tube 6 of the arrangement device 3, thereby putting the tissue closing device 1 into a usable state.

In addition, by moving the proximal part 9 (the casing 11) in the proximal direction (one direction), all the steps (operations) can be carried out to effect deformation of the deformation part 42 and release of the clip 4 without need for the operator's (user's) special operation. As a result, a wound hole can be closed with the clip 4, and the clip 4 can be disposed (left indwelling) in the living body. Therefore, the tissue closing device 1 can be relatively easily operated even by only one hand, and the staunching work for a wound hole formed in a tissue membrane such as a blood vessel wall can be performed relatively easily, speedily and assuredly. Specifically, the wound hole can be closed (closed up) relatively easily, speedily and assuredly to achieve quite good staunching (hemostasis).

Particularly, since the deformation part 42 of the clip 4 is deformed by the restoring forces of the coil springs 22, there is no need for a manual operation of deforming the deformation part 42 of the clip 4. A predetermined fastening force can always be obtained so that a wound hole can be closed extremely easily, speedily and assuredly.

Further, in the condition where the deformation part 42 of the clip 4 has been brought into a desired form between the first form and the second form, the condition can be maintained by the thread 46. This makes it possible to cope with various conditions (statuses) of tissue membrane.

FIGS. 19-26 illustrate aspects of a second embodiment of the tissue closing device, specifically a different retaining member and the surroundings thereof.

To simplify the illustrations and avoid complicated drawings, the fixing tube is omitted in FIGS. 20-22 and FIGS. 24-26. In addition, the sheath is omitted in FIGS. 21, 22 and 24-26.

In addition, for convenience of description, in FIGS. 19-26, the direction of the arrow A is referred to as the "distal" direction, the direction of the arrow B is referred to as the "proximal" direction, the direction of the arrow C is referred to as the "upward" or "upper" direction, and the direction of the arrow D is referred to as the "downward" or "lower" direction.

The description below will focus primarily on differences between this embodiment and the first embodiment described above. Features in this embodiment that are the same as in the first embodiment are designated by like reference numerals, and a detailed description of such features is not repeated.

The tissue closing device 1 in the second embodiment is the same as in the first embodiment above, except for the configuration of the retaining member 18. In short, in the retaining member 18 according to the first embodiment above, the portion for compressing the deformation part 42 of the clip 4 in the radial direction of the cover tube 6 as compared to the state in the initial condition (the condition immediately upon assembly) and the portion for inclining (folding) the seal part 41 of the clip 4 are provided at the same position (in common). In the retaining member 18 according to the second embodiment, the compressing part (a pair of clamp pieces 122) for compressing the deformation part 42 of the clip 4 in the radial direction of the cover tube 6 as compared to the state in the initial condition and the portion for inclining (folding) the seal part 41 of the clip 4 are provided at different positions axially spaced from one another. Specifically, in the second embodiment of the retaining member 18, the portion for inclining the seal part 41 is located (arranged) on the distal side relative to the compressing part.

Figure 19:
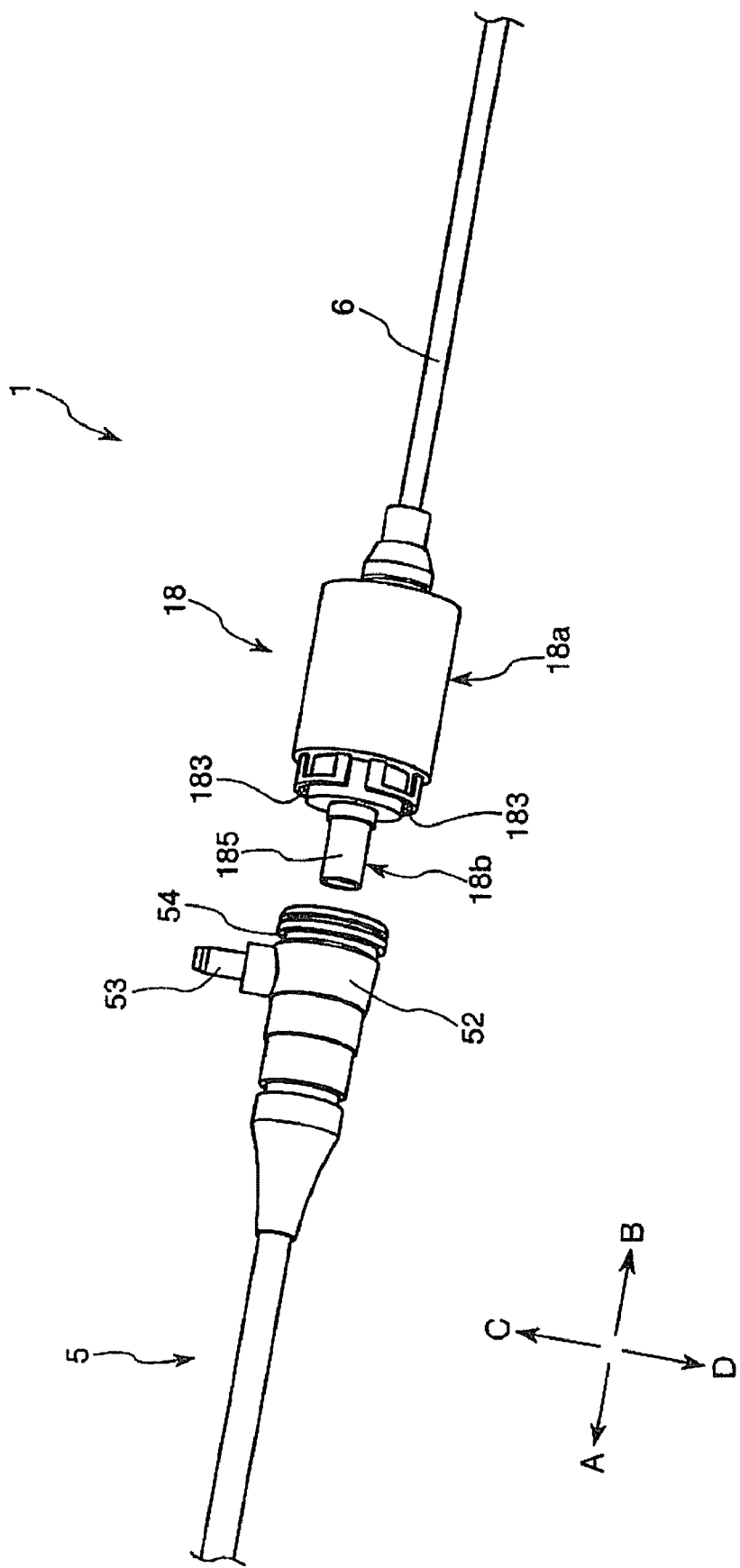
FIG. 19 is a perspective view of a retaining member and the surroundings thereof in a second embodiment of the tissue closing device disclosed here.
Figure 20:
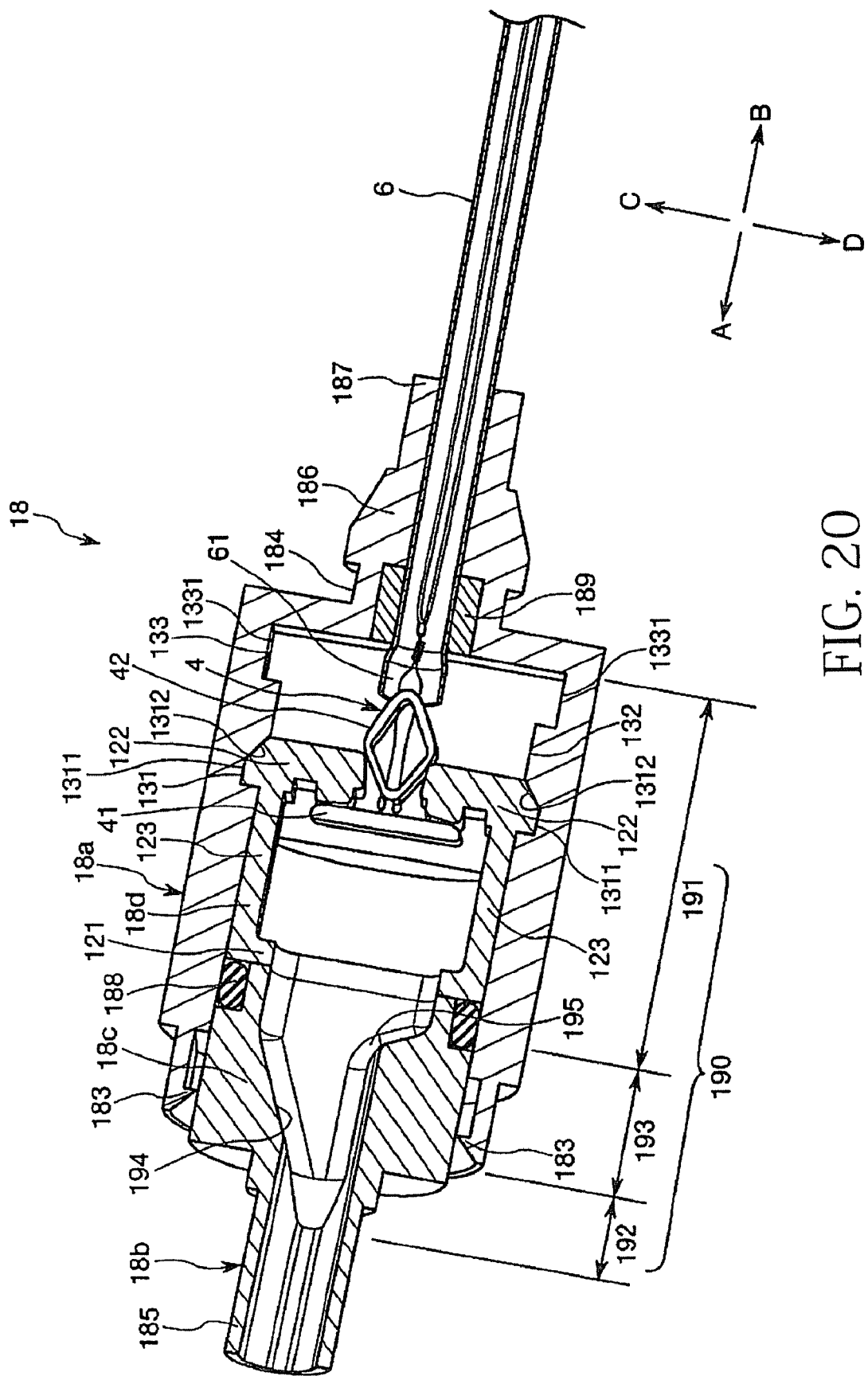
FIG. 20 is a cross-sectional perspective view of the retaining member of the tissue closing device shown in FIG. 19.

As shown in FIGS. 19 and 20, in the tissue closing device 1 according to the second embodiment, the retaining member 18 is composed of a proximal-side member 18a, a distal-side member 18b disposed on the distal side of the proximal-side member 18a and movable relative to the proximal-side member 18a in the proximal direction, and a seal member (sealing means) 188 for liquid-tight (gas-tight) sealing between the proximal-side member 18a and the distal-side member 18b. The distal-side member 18b is positioned in the inside (inner peripheral side) of the proximal-side member 18a. A seal member (sealing means) 189 for providing a liquid-tight (gas-tight) seal between the proximal-side member 18a and the cover tube 6 may be additionally provided.

The distal-side member 18b includes a body portion 18c disposed on the distal side, and a proximal-side portion 18d disposed on the proximal side. The body portion 18c and the proximal-side portion 18d are integrated with each other by firmly attaching (e.g., adhesion with an adhesive, welding or the like) to each other. The body portion 18c and the proximal-side portion 18d may be formed integrally as a single unitary one piece part.

The body portion 18c of the distal-side member 18b includes a narrow space part 192, a transition part 193 and part of a wide space part 191, which are components of an accommodating part 190, as well as a tubular portion 185. The transition part 193 has an inclined surface 194 on the upper side in FIG. 20. The inclined surface 194 is so inclined as to be located on the upper side in FIG. 20 on the proximal side than on the distal side. In addition, the transition part 193 has a stepped portion 195 on the lower side in FIG. 20 at a proximal portion thereof. The stepped portion 195 is rounded.

The narrow space part 192 and the transition part 193 of the accommodating part 190 are portions for inclining (folding) the seal part 41 of the clip 4, and are located on the distal side relative to a pair of clamp pieces 122 which will be described later.

The proximal-side portion 18d of the distal-side member 18b includes: a base portion 121 constituting a part of the wide space part 191; the pair of clamp pieces 122 which can be urged toward and away from each other, can clamp the deformation part 42 of the clip 4 therebetween, and thus serve as a compressing part for compressing the deformation part 42 of the clip 4 in the radial direction of the cover tube 6 as compared to the initial condition, attendantly on movement of the distal-side member 18b relative to the proximal-side member 18a toward the proximal side; and a pair of leg parts 123 which connect the base portion 121 and the pair of clamp pieces 122 to each other and which are elastically deformable.

The base portion 121 is a circular ring-shaped (annular-shaped) portion, and is firmly attached on the distal side thereof to the proximal side of the body portion 18c.

The two leg parts 123 are each rod-shaped or plate-shaped, and are so disposed that the longitudinal direction thereof coincides with the longitudinal direction (axial direction) of the cover tube 6 and that they face each other with the center axis (axis) of the cover tube 6 therebetween. In the initial condition, the leg parts 123 are each in a natural state (in the condition where no external force is exerted thereon).

The two clamp pieces 122 are provided at proximal portions of the pair of leg parts 123, and are so disposed that they face each other with the center axis of the cover tube 6 therebetween. The pair of clamp pieces 122 clamp the deformation part 42 of the clip 4 therebetween as the clamp pieces are deformed toward each other.

In the initial condition, a distal-side portion of the deformation part 42 of the clip 4 is located between the pair of clamp pieces 122, while the seal part 41 is located on the distal side relative to the clamp pieces 122 and is in contact with the distal-side surfaces of the clamp pieces 122 (see FIG. 20). When the two clamp pieces 122 are deformed toward each other, the deformation part 42 of the clip 4 is clamped therebetween, and the deformation part 42 is compressed in a radial direction of the cover tube 6 as compared to its state in the initial condition (see FIG. 21).

The gap distance (spacing) between the pair of clamp pieces 122 in the initial condition is so set that such a slight load as not to cause any problem is exerted, or no load is exerted at all, on the deformation part 42 of the clip 4 from the pair of clamp pieces 122. Specifically, the gap distance (spacing) is so set that a load for compressing the deformation part 42 of the clip 4 in a radial direction of the cover tube 6 as compared to the form in the natural state thereof (the condition where no external force is exerted thereon) is slightly exerted on the deformation part 42 from the pair of clamp pieces 122 to such an extent as not to cause any problem, whereby the deformation part 42 is slightly folded in a compressed manner in the radial direction of the cover tube 6, or that no load is exerted on the deformation part 42 from the pair of clamp pieces 122 and, hence, the deformation part 42 is not deformed at all.

This makes it possible to inhibit or prevent the deformation part 42 (the clip 4) from acquiring a semi-permanently set shape, and to prevent the deformation part 42 (the clip 4) from being deteriorated or broken.

More specifically, the gap distance between the pair of clamp pieces 122 in the initial condition is preferably set so that the length of the deformation part 42 in the radial direction of the cover tube 6 in the initial condition is about 50 to 100%, more preferably about 70 to 100%, based on the length of the deformation part 42 in the radial direction of the cover tube 6 in the natural state.

The proximal-side member 18a has the most part of the wide space part 191 of the accommodating part 190. That is, more than half of the wide space part 191 is located in the proximal-side member 18a. The proximal-side member 18a further has a pair of ribs (claws) 183 at a distal portion, and a groove 184 on the proximal side of the wide space part 191. The ranges (positions) of the wide space part 191, the transition part 193 and the narrow space part 192 of the accommodating part 190 vary depending on the positional relationship between the proximal-side member 18a and the distal-side member 18b (see FIGS. 20 and 22).

The wide space part 191 of the proximal-side member 18a includes: an initial accommodating part 131 for accommodating the pair of clamp pieces 122 in the initial condition; a clamping condition maintaining part 132 provided on the proximal side of the initial accommodating part 131 for maintaining the condition in which the pair of clamp pieces 122 clamp the deformation part 42 of the clip 4 therebetween; and a compression canceling part (clamping canceling part) 133 on the proximal side of the clamping condition maintaining part 132 and accommodating the pair of clamp pieces 122. The initial accommodating part 131, the clamping condition maintaining part 132 and the compression canceling part 133 are arranged in a continuous form, meaning the clamping condition maintaining part 132 follows right after the initial accommodating part 131, and the compression canceling part 133 follows right after the clamping condition maintaining part 132, in the proximal direction. A proximal portion of the wide space part 191 constitutes the compression canceling part 133.

The initial accommodating part 131 has a pair of recesses 1311 formed in an inner peripheral portion of the proximal-side member 18a. The recesses 1311 are respectively provided, at their inner surfaces on the proximal side, with inclined surfaces 1312 capable of making contact with the corresponding clamp pieces 122. The inclined surface 1312 on the upper side in FIG. 20 is so inclined as to be located on the lower side in FIG. 20 on the proximal side than on the distal side, while the inclined surface 1312 on the lower side in FIG. 20 is so inclined as to be located on the upper side in FIG. 20 on the proximal side than on the distal side. In other words, the inclined surfaces 1312 are so inclined that the spacing between the inclined surfaces 1312 gradually decreases along the direction from the distal side toward the proximal side.

In addition, the compression canceling part 133 has a pair of recesses 1331 formed in an inner peripheral portion of the proximal-side member 18a.

In the initial condition, the clamp pieces 122 are contained in the initial accommodating part 131, and the leg parts 123 are each in the natural state (see FIG. 20). Specifically, an upper-side end portion of the clamp piece 122 on the upper side and a lower-side end portion of the clamp piece 122 on the lower side are respectively positioned in the recesses 1311. This helps ensure that the distal-side member 18b is permitted to move relative to the proximal-side member 18a toward the proximal side but is inhibited from moving toward the distal side.

Figure 21:
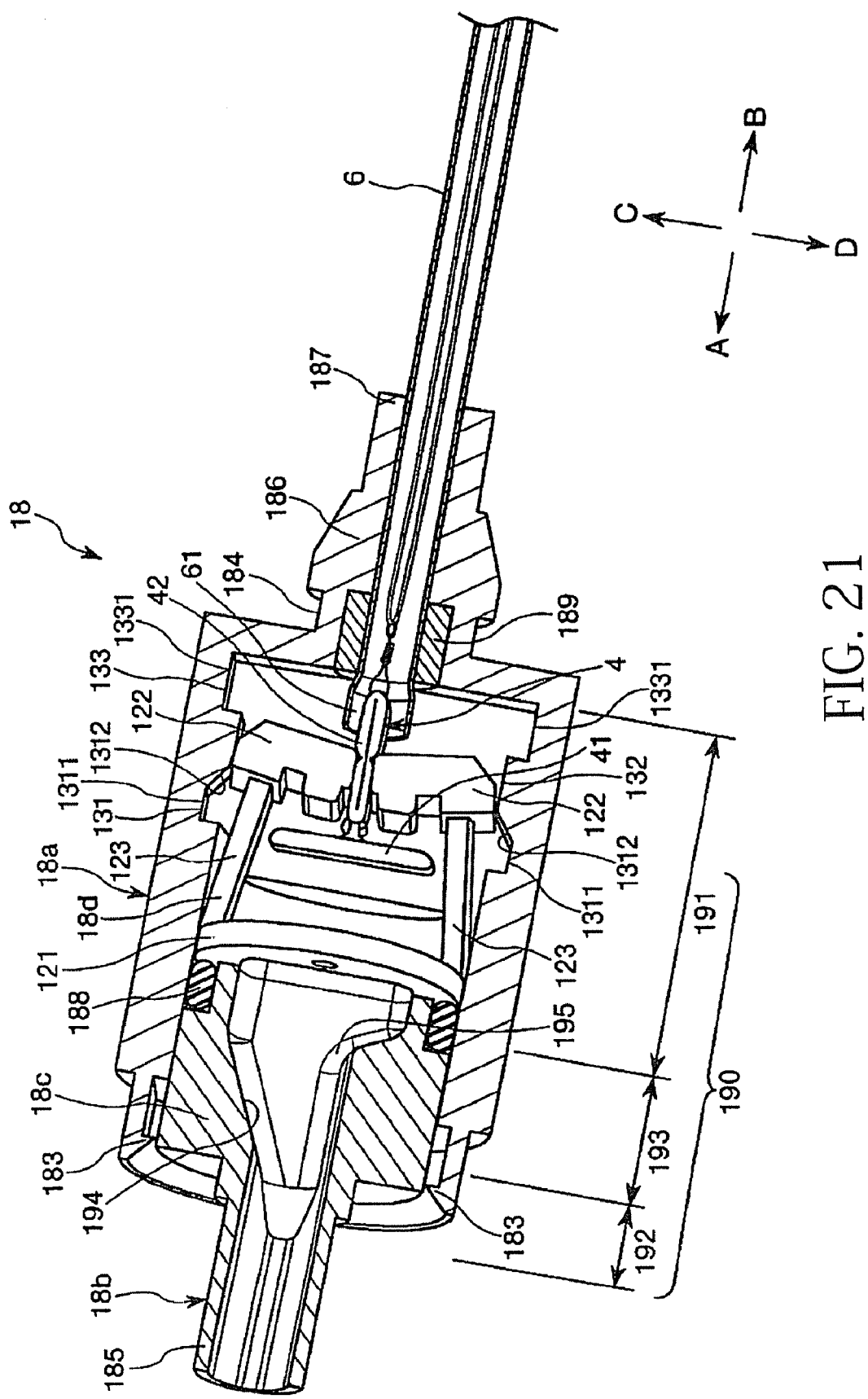
FIG. 21 is a cross-sectional perspective view of the tissue closing device shown in FIG. 19 illustrating operational aspects of the tissue closing device.

When the distal-side member 18b is moved relative to the proximal-side member 18a toward the proximal side starting from the initial condition, the clamp pieces 122 are deformed to approach each other along the pair of inclined surfaces 1312, to clamp the deformation part 42 of the clip 4 therebetween as shown in FIG. 21. In this case, the leg parts 123 are elastically deformed.

When the distal-side member 18b is further moved relative to the proximal-side member 18a toward the proximal side, the condition in which the pair of clamp pieces 122 are clamping the deformation part 42 therebetween is maintained by the clamping condition maintaining part 132 during the movement, and the deformation part 42 is pushed into the opening part 61 of the cover tube 6 (see FIG. 21).

Figure 22:
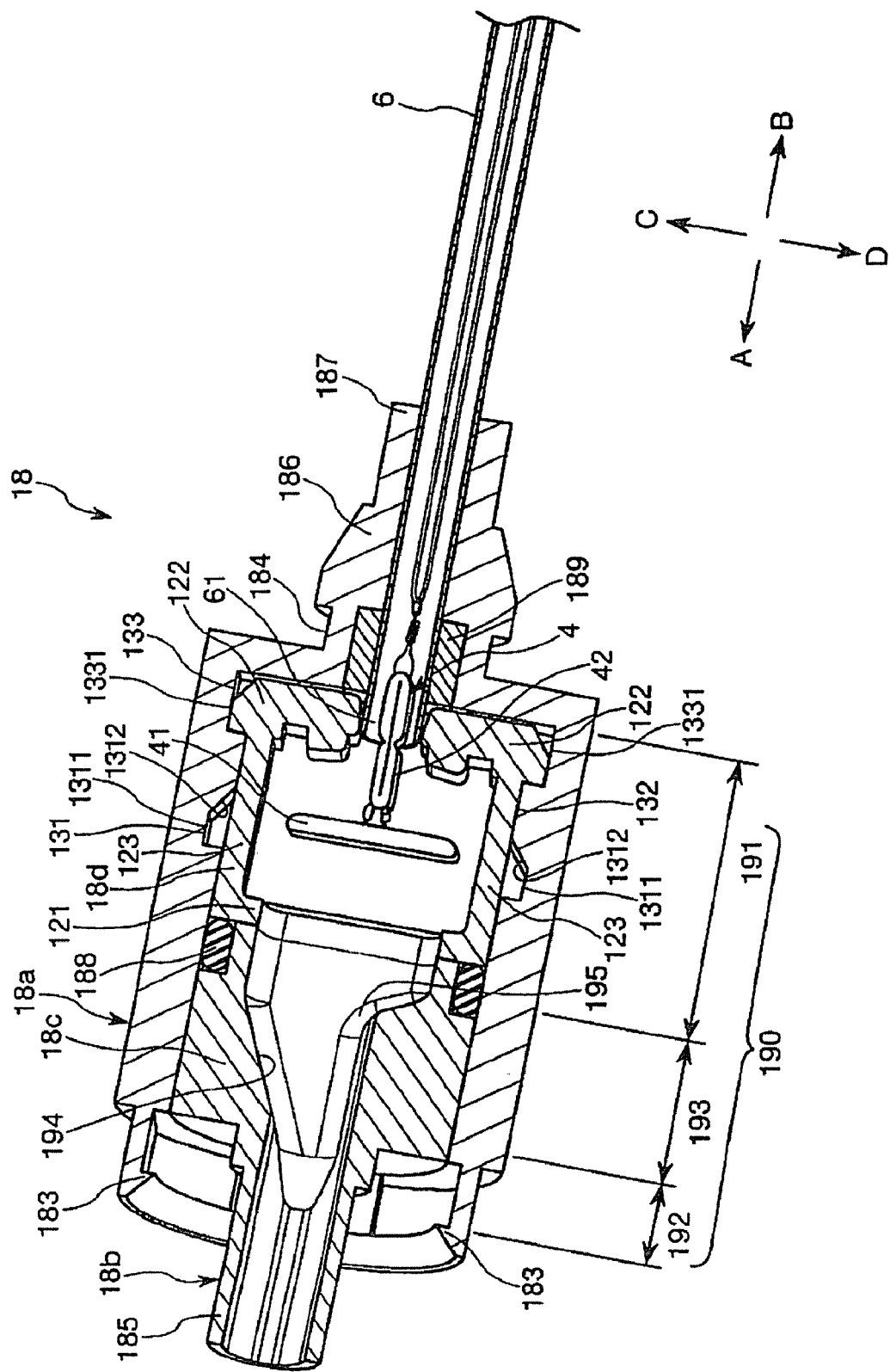
FIG. 22 is a cross-sectional perspective view of the tissue closing device shown in FIG. 19 illustrating another operational aspect of the tissue closing device.

When the distal-side member 18b is further moved relative to the proximal-side member 18a toward the proximal side, the clamp pieces 122 are contained in the compression canceling part 133 as illustrated in FIG. 22. Specifically, the upper-side end portion of the clamp piece 122 on the upper side and the lower-side end portion of the clamp piece 122 on the lower side are respectively positioned in the recesses 1331. This results in the clamp pieces 122 being deformed away from each other by the resilient forces (restoring forces) of the pair of leg parts 123, to release the deformation part 42, and the leg parts 123 return to their natural state.

In addition, since the end portions of the clamp pieces 122 are respectively positioned in the recesses 1331, the positional relation between the distal-side member 18b and the proximal-side member 18a is fixed, resulting in that the distal-side member 18b and the proximal-side member 18a can be moved as one body. In other words, the two clamp pieces 122 are inhibited from returning to the clamping condition maintaining part 132. Accordingly, the recesses 1331 of the compression canceling part 133 constitute a part of a movement inhibitive means by which the clamp pieces 122 contained in the compression canceling part 133 are inhibited from returning to the clamping condition maintaining part 132.

The seal member 188 is composed of an elastic body having, for example, a circular ring-shaped or annular-shaped form. The seal member 188 is disposed in a groove formed in an outer peripheral portion of the distal-side member 18b between the body portion 18c and the proximal-side portion 18d, is located between the inner peripheral surface of the proximal-side member 18a and the outer peripheral surface of the distal-side member 18b, and is in firm contact with both the inner peripheral surface of the proximal-side member 18a and the outer peripheral surface of the distal-side member 18b. As a result, liquid-tight (gas-tight) sealing is established between the inner peripheral surface of the proximal-side member 18a and the outer peripheral surface of the distal-side member 18b, whereby leakage of blood is prevented from occurring there.

In addition, the seal member 189 is composed of an elastic body having a cylindrical (tubular) shape, for example. The seal member 189 is disposed in a groove formed in an inner peripheral portion of the proximal-side member 18a in the vicinity of the groove 184, is located between the inner peripheral surface of the proximal-side member 18a and the outer peripheral surface of the cover tube 6, and is in firm contact with both the inner peripheral surface of the proximal-side member 18a and the outer peripheral surface of the cover tube 6. As a result, a liquid-tight (gas-tight) sealing is established between the inner peripheral surface of the proximal-side member 18a and the outer peripheral surface of the cover tube 6, whereby leakage of blood is prevented from occurring there.

The liquid-tight (gas-tight) sealing between the inner peripheral surface of the proximal-side member 18a and the outer peripheral surface of the cover tube 6 may also be achieved by partly narrowing the inner peripheral surface of the proximal-side member 18a to reduce the clearance between this inner peripheral surface and the outer peripheral surface of the cover tube 6, instead of providing the seal member 189.

The respective materials constituting the seal members 188, 189 are not particularly limited. Examples of the materials which can be used here include elastic materials such as natural rubber and various synthetic rubbers, e.g., isoprene rubber, silicone rubbers, urethane rubber, styrene-butadiene rubber, fluororubbers, acrylic rubber, etc., various thermoplastic elastomers such as polyamide-based ones and polyester-based ones, etc., porous materials such as foamed materials, etc.

The outer dimension of the distal portion of the cover tube 6 is greater than the inner dimension of the hole in the seal member 189 and, in the initial condition, the distal portion is located inside the wide space part 191 in proximity to the seal member 189. This helps ensure that, in the initial condition, the cover tube 6 is permitted to move relative to the proximal-side member 18a toward the distal side but is inhibited from moving toward the proximal side.

The operation of the tissue closing device 1 according to this second embodiment will now be described below, focusing primarily on differences relative to the first embodiment.

First, the operator (user) connects the retaining member 18 to the hub 52 of the sheath 5. In this case, as shown in FIG. 19, the tubular portion 185 of the retaining member 18 is inserted into the hub 52 through the hemostatic valve of the hub 52, and the hub 52 is pushed into the inside of a distal portion of the retaining member 18. In this step, the distal-side member 18b is moved relative to the proximal-side member 18a toward the proximal side, starting from the initial condition shown in FIG. 20. Also, before the retaining member 18 and the hub 52 are connected, the clip 4 is positioned in the retaining member 18 in the manner shown in FIG. 20.

When the distal-side member 18b is moved relative to the proximal-side member 18a toward the proximal side, first, as shown in FIG. 21, the pair of clamp pieces 122 are deformed toward each other along the pair of inclined surfaces 1312, to form a narrowed space part in which the deformation part 42 of the clip 4 is clamped. As a result, the deformation part 42 is compressed in a radial direction of the cover tube 6 as compared with its state in the initial condition, to become easier to push into the opening part 61 of the cover tube 6. In addition, the pair of leg parts 123 are deformed elastically. Then, while the condition in which the clamp pieces 122 are clamping the deformation part 42 therebetween is maintained by the clamping condition maintaining part 132, the deformation part 42 is pushed (inserted) into and retained in the opening part 61 of the cover tube 6.

Figure 23:
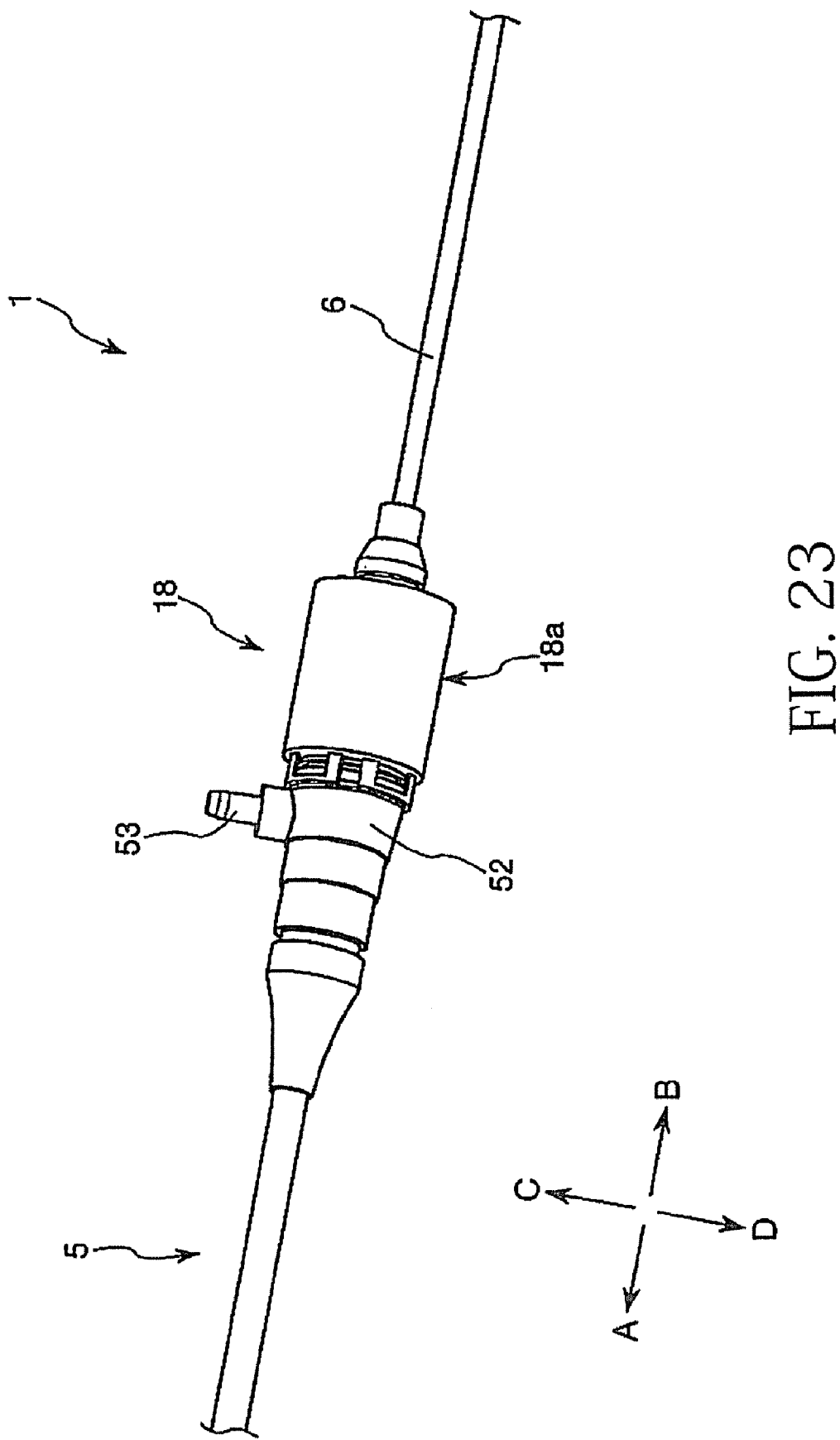
FIG. 23 is a perspective view of the tissue closing device shown in FIG. 19 showing other operational aspects of the tissue closing device.

Next, as shown in FIG. 22, the two clamp pieces 122 are contained or positioned in the compression canceling part 133, where the clamp pieces 122 are deformed away from each other by the resilient forces (restoring forces) of the pair of leg parts 123 to release the deformation part 42, whereby the leg parts 123 each return to the natural state. As a result, the positional relation between the distal-side member 18b and the proximal-side member 18a is fixed, so that the distal-side member 18b and the proximal-side member 18a can be moved together as a single unit. In addition, the ribs 183 of the retaining member 18 are inserted into the groove 54 in the hub 52, and are engaged with the surfaces inside the groove 54. Consequently, the retaining member 18 and the hub 52 of the sheath 5 are connected to each other as shown in FIG. 23, and this condition is maintained.

In this manner, transition is made from the condition where the clip 4 is contained in the accommodating part 190 of the retaining member 18 to the condition where the deformation part 42 of the clip 4 is retained in the opening part 61 of the cover tube 6.

Figure 24:
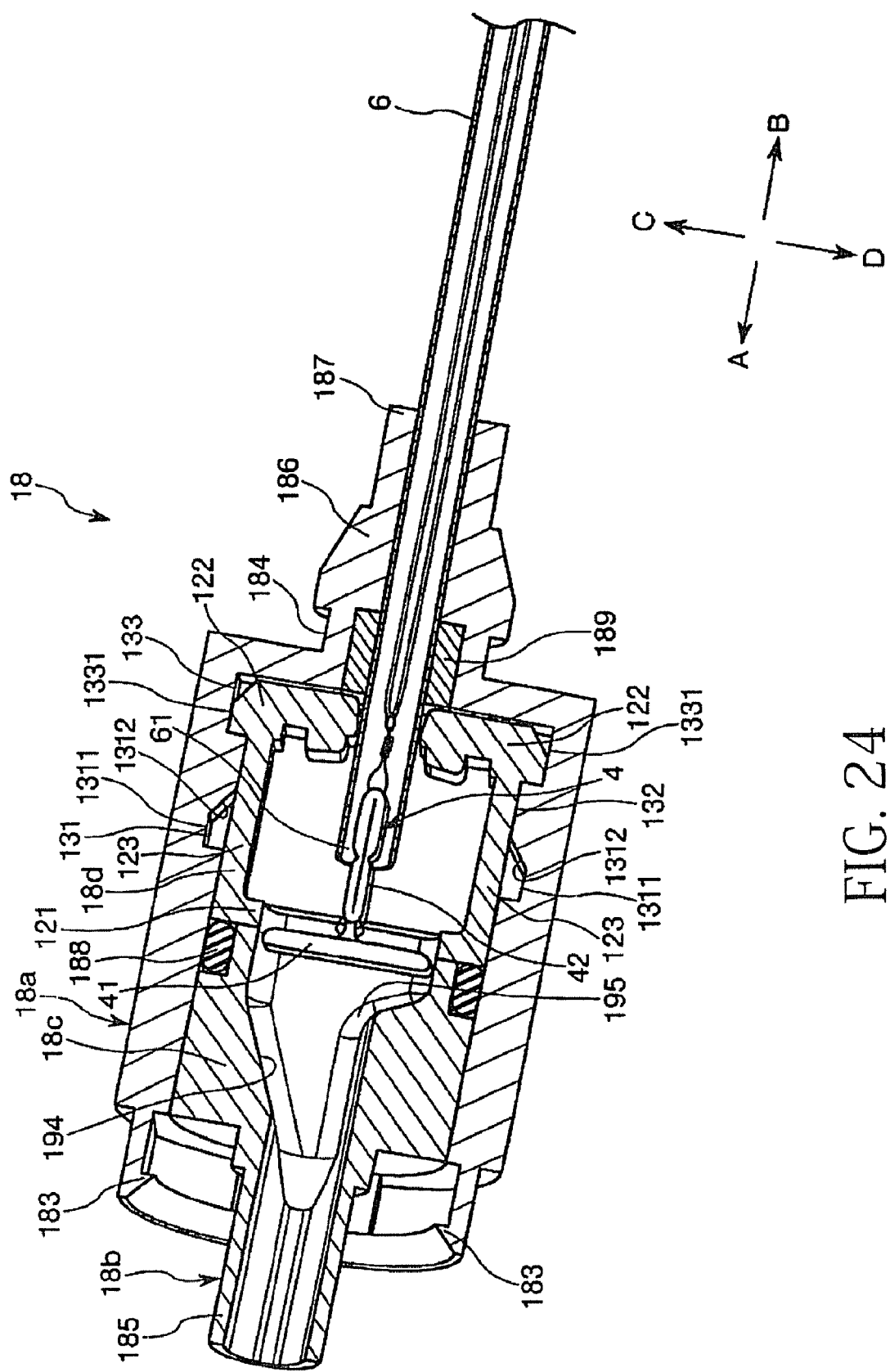
FIG. 24 is a cross-sectional perspective view of the tissue closing device shown in FIG. 19 illustrating operational aspects of the tissue closing device.

Next, as shown in FIG. 24, the sheath 5 and the retaining member 18 are moved relative to the cover tube 6 toward the proximal side, i.e., moved toward the proximal side along the cover tube 6.

Figure 25:
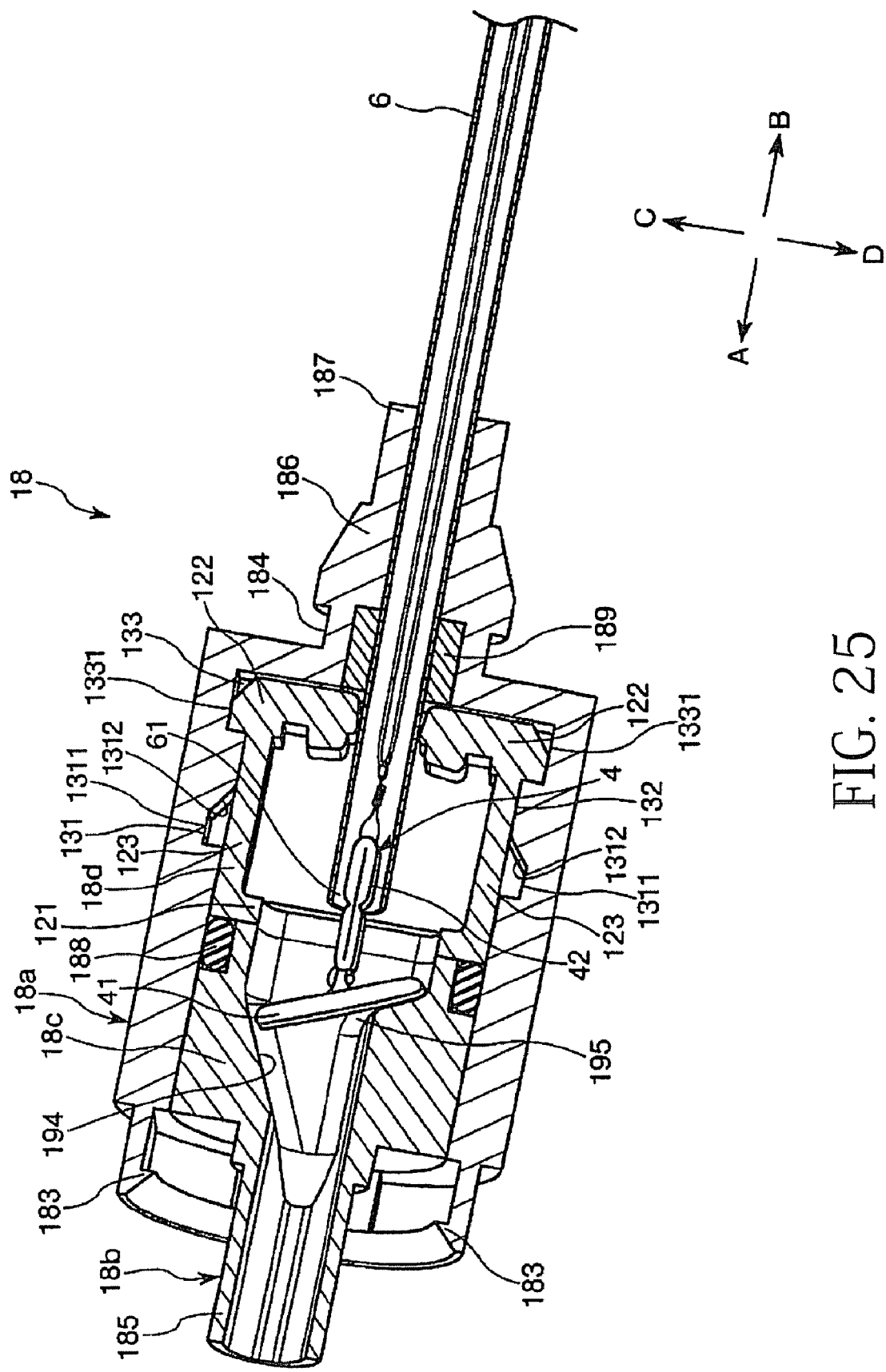
FIG. 25 is a cross-sectional perspective view of the tissue closing device shown in FIG. 19 illustrating operational aspects of the tissue closing device.

This results in a lower-side portion of the seal part 41 of the clip 4 coming into contact with the stepped portion 195 of the transition part 193, and then the seal part 41 is gradually inclined (folded) along the inclined surface 194 as shown in FIG. 25.

Figure 26:
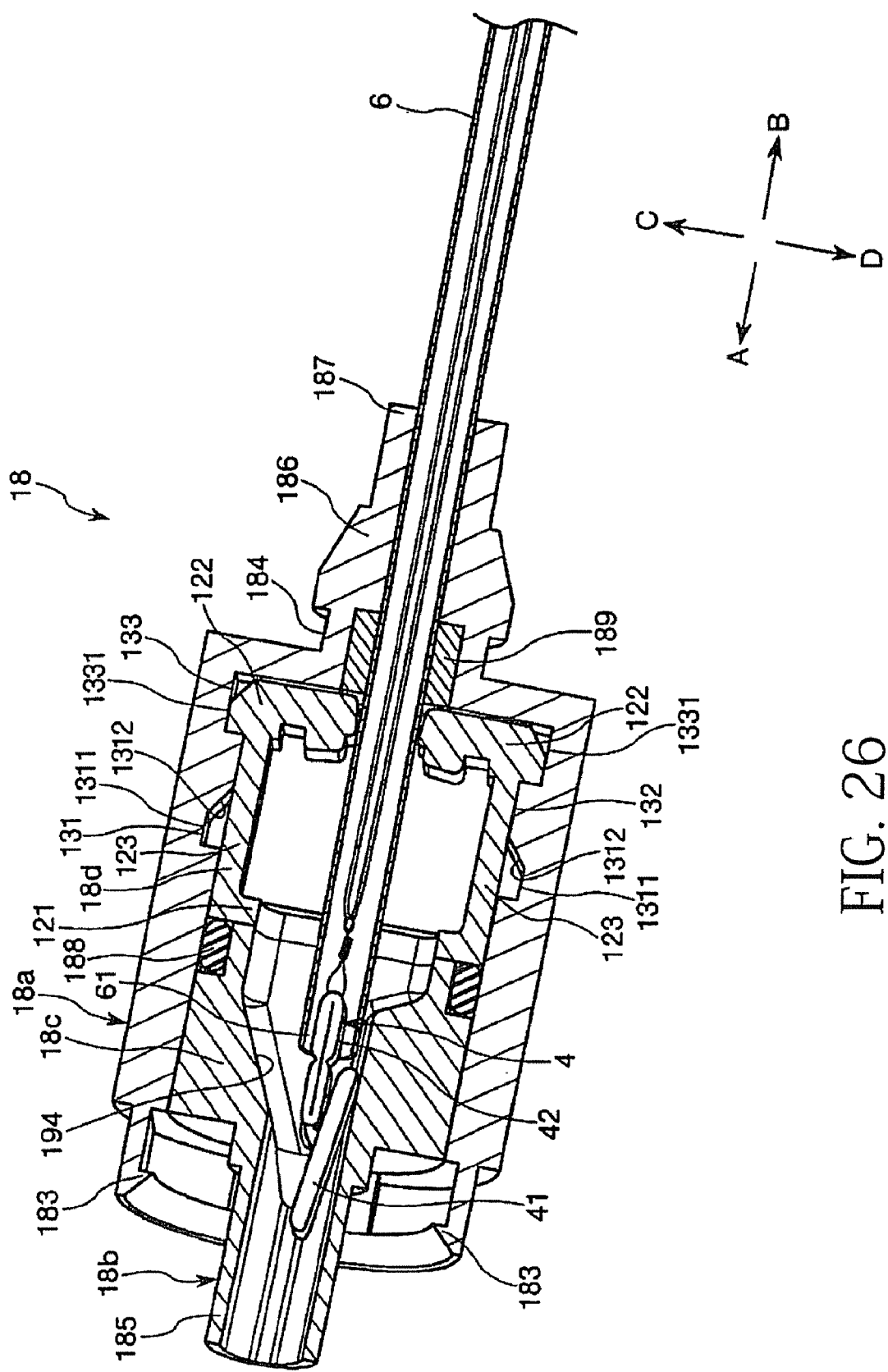
FIG. 26 is a cross-sectional perspective view of the tissue closing device shown in FIG. 19 illustrating operational aspects of the tissue closing device.

Then, as shown in FIG. 26, the seal part 41 of the clip 4 is inserted into the narrow space part 192, whereon the seal part 41 is further inclined (folded). Consequently, the clip 4 is folded completely.

Subsequently, the sheath 5 and the retaining member 18 are further moved relative to the cover tube 6 toward the proximal side, whereon the clip 4 is passed through the lumen of the tubular portion 185, is discharged from the retaining member 18, and is inserted into the through-hole 51 of the sheath 5. The subsequent process is the same as in the first embodiment above, so the description thereof is not repeated again According to the present tissue closing device 1, the same advantageous effects as those in the first embodiment described above are achieved.

According to this tissue closing device 1, first, the deformation part 42 of the clip 4 is clamped between the pair of clamp pieces 122, to be thereby compressed in the radial direction of the cover tube 6 as compared to its form in the initial condition. The thus compressed deformation part 42 is pushed into the opening part 61 of the cover tube 6. Therefore, the deformation part 42 can be retained in the opening part 61 of the cover tube 6 more smoothly and assuredly and in an appropriate state (in the state of being in the appropriate posture or orientation).

In addition, the seal part 41 is inclined and folded in the condition where the deformation part 42 is retained in the opening part 61 of the cover tube 6. Therefore, the clip 4 can be folded more smoothly and assuredly.

While the tissue closing device has been described based on the embodiments shown in the drawings and described above, the present invention is not limited to these embodiments, and the configurations of the components or parts can be replaced by those having similar or equivalent functions. Also, other components may be added to the tissue closing device.

The tissue closing device may also be embodied as a combination of two or more configurations (features) of the embodiments described above.

In the first embodiment described above, the retaining member 18 is so configured that the whole part of the retaining member 18 is movable relative to the cover tube (elongated part) 6 toward the proximal side, and, actually, the whole part of the retaining member 18 is moved relative to the cover tube 6 toward the proximal side in such a manner that, starting from the condition where the clip (closure) 4 is retained in the retaining member 18, the deformation part 42 of the clip 4 is pushed into the opening part 61 of the cover tube 6, resulting in the condition where the deformation part 42 of the clip 4 is retained in a distal portion of the cover tube 6. In the second embodiment described above, the retaining member 18 is so configured that the whole part of the retaining member 18 is movable relative to the cover tube 6 toward the proximal side, and, actually, a part of the retaining member 18 is moved relative to the cover tube 6 toward the proximal side in such a manner that, starting from the condition where the clip 4 is retaining in the retaining member 18, the deformation part 42 of the clip 4 is pushed into the opening part 61 of the cover tube 6, resulting in the condition where the deformation part 42 of the clip 4 is retained in a distal portion of the cover tube 6. However, the tissue closing device disclosed here is not limited to these configurations. For instance, the retaining member 18 may be so configured that a part of the retaining member 18 is movable relative to the cover tube 6 toward the proximal side, and, actually, a part of the retaining member 18 is moved relative to the cover tube 6 toward the proximal side in such a manner that, starting from the condition where the clip 4 is retained in the retaining member 18, the deformation part 42 of the clip 4 is pushed into the opening part 61 of the cover tube 6, resulting in the condition where the deformation part 42 of the clip 4 is retained in a distal portion of the cover tube 6.

In the embodiments described above, a configuration has been adopted in which one of the two end portions of the thread 8 is fixed in the proximal part 9, whereas the other is uncoupled. However, a configuration may be adopted in which both end portions of the thread 8 are uncoupled simultaneously. In such a configuration, the thread 8 is left on the living body side while remaining connected to the clip 4. Thereafter, the thread 8 can be removed as desired, by an operator's manual procedure.

The cancellation (trigger means) of the restraint for holding the coil springs (first elastic members) 22 in the deformed state (active state) may be performed, for example, by an operation of a switch or button. Further, the configuration of the arrangement device may be a configuration other than the configuration described above.

The principles, embodiments and modes of operation of the tissue closing device disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A tissue closing device comprising:
    a closure configured to close a hole penetrating a tissue membrane of a living organism; and
    an arrangement device which retains the closure for delivery to the hole of the tissue membrane and positions the closure at the hole of the tissue membrane to close the hole with the closure;
    the closure comprising:
        a seal part for covering, from one side surface of the tissue membrane, the hole penetrating the tissue membrane and a peripheral part of the hole; and
        a deformable deformation part;
    the arrangement device comprising:
        an elongated part comprising, at a distal portion of the elongated part, an opening part configured to retain the deformation part of the closure and to penetrate the hole in the tissue membrane;
        a retaining member located at the distal portion of the elongated part in an initial condition of the retaining member, the retaining member retaining the closure in an initial condition, at least a part of the retaining member being movable relative to the elongated part in a proximal direction; and
        the at least a part of the retaining member being movable relative to the elongated part in the proximal direction to push the deformation part of the closure into the opening part of the elongated part to thereby make a transition from the initial condition in which the closure is retained in the retaining member to a condition in which the deformation part of the closure is retained at the distal portion of the elongated part;
    wherein:
        the retaining member comprises a proximal-side member and a distal-side member, the distal-side member of the retaining member being positioned on a distal side of the proximal-side member and movable relative to the proximal-side member; and
        the distal-side member comprises a compressing part by which the deformation part of the closure is compressed in a radial direction of the elongated part, as the distal-side member is moved relative to the proximal-side member, as compared to a configuration of the closure in the initial condition.

2. The tissue closing device as set forth in claim 1, wherein the retaining member comprises an accommodating part including a wide space part defining a first space, a narrow space part on a distal side relative to the wide space part and defining a second space narrower than the space of the wide space part, and a transition part between the wide space part and the narrow space part defining a third space; and
    wherein the closure is adapted to be at least partially positioned in the wide space part in the initial condition, and moved to the narrow space part when the retaining member is moved relative to the elongated part in the proximal direction toward a proximal side.

3. The tissue closing device as set forth in claim 2, wherein the transition part includes an inclined surface, and the closure is adapted to gradually fold as the closure moves along the inclined surface when the retaining member is moved relative to the elongated part toward the proximal side.

4. The tissue closing device as set forth in claim 2, further comprising a sheath possessing a proximal portion connectable to the retaining member, the sheath being usable with the elongated part inserted in a lumen of the sheath and with the sheath connected to the retaining member.

5. The tissue closing device as set forth in claim 4, wherein a distal end portion of the retaining member and a proximal end portion of the sheath comprise a first connecting part to connect together the retaining member and the sheath so that the retaining member and the sheath move together relative to the elongated part in the proximal direction when the retaining member is moved relative to the elongated part in the proximal direction.

6. The tissue closing device as set forth in claim 5, wherein the arrangement device comprises a proximal part on the proximal side of the elongated part, the retaining member and the proximal part comprising a second connecting part to connect the retaining member and the proximal part, the retaining member being movable relative to the elongated part toward the proximal side to effect connection between the retaining member and the proximal part by the second connecting part.

7. The tissue closing device as set forth in claim 5, wherein the retaining member comprises a tubular part projecting at a distal portion of the retaining member, the tubular part possessing a lumen communicating with the second space in the narrow space part, the tubular part adapted to be inserted into a proximal end portion of the sheath to effect communication between the lumen of the tubular part and the lumen of the sheath, the closure which is retained at a distal portion of the elongated part adapted to be passed through the lumen of the tubular part such that the closure is inserted into the lumen of the sheath when the retaining member is moved relative to the elongated part toward the proximal side.

8. The tissue closing device as set forth in claim 1, wherein:
    the retaining member also comprises a part located on a distal side relative to the compressing part and which folds the seal part of the closure as the closure moves through the retaining member.

9. The tissue closing device as set forth in claim 1, wherein when the distal-side member is moved relative to the proximal-side member toward the proximal side, the compressing part is adapted to clamp the deformation part from both sides of the deformation part, whereby the deformation part is compressed in a radial direction of the elongated part, and the deformation part is pushed into the opening part.

10. The tissue closing device as set forth in claim 1, wherein the compressing part comprises a pair of deformable clamp pieces adapted to be deformed toward and away from each other, the pair of clamp pieces being adapted to clamp the deformation part between the clamp pieces when the clamp pieces are deformed toward each other while the deformation part is positioned between the clamp pieces.

11. The tissue closing device as set forth in claim 10, wherein:
the proximal-side member comprises a pair of inclined surfaces adapted to contact the pair of clamp pieces when the distal-side member is moved relative to the proximal-side member toward the proximal side; and
the pair of clamp pieces are deformed inwardly toward each other when the clamp pieces engage the inclined surfaces during movement of the distal-side member relative to the proximal-side member toward the proximal side.

12. The tissue closing device as set forth in claim 11, wherein:
the proximal-side member comprises, on the proximal side of the pair of inclined surfaces, a clamping state retaining part for retaining the deformation part in a clamped state between the pair of clamp pieces; and
wherein the deformation part is adapted to be pushed into the opening part when the distal-side member is moved relative to the proximal-side member toward the proximal side.

13. The tissue closing device as set forth in claim 12, wherein:
the proximal-side member comprises, on the proximal side of the clamping state retaining part, a compression canceling part for accommodating the pair of clamp pieces;
the pair of clamp pieces comprises a pair of elastically deformable leg parts; and
wherein, when the pair of leg parts is contained in the compression canceling part, the leg parts are adapted to be deformed away from each other by resilient forces of the leg parts so as to thereby release the deformation part.

14. The tissue closing device as set forth in claim 13, further comprising movement inhibitive means for inhibiting the leg parts contained in the compression canceling part from returning into the clamping state retaining part.

15. A tissue closing device comprising:
a closure configured to close a hole passing though a tissue membrane of a living organism; and
an arrangement device adapted to retain the closure for delivery to the hole in the tissue membrane and position the closure at the hole in the tissue membrane;
the closure comprising:
a seal part positionable on one side surface of the tissue membrane to cover the hole penetrating the tissue membrane and a peripheral part of the hole; and
a deformable deformation part connected to the seal part and deformable from an initial condition to a deformed condition positionable on a side surface of the tissue membrane opposite the one side surface so that the tissue membrane is sandwiched between the seal part and the deformation part;
the arrangement device comprising:
an elongated part comprising a lumen and a distally located opening part configured to retain the deformation part of the closure and to penetrate the hole in the tissue membrane; and
a retaining member having an interior communicating with the lumen of the elongated part, the closure being positionable in the interior of the retaining member in an initial condition of the closure, the interior of the retaining member comprising a narrowed space part,
wherein the interior of the retaining member further comprises an inclined surface, whereby the closure is adapted to move along the inclined surface so as to incline the seal part relative to the deformation part; and
wherein the retaining member comprises a distal-side member radially movable relative to a proximal-side member, and a second inclined surface is located on the proximal-side member.

16. The tissue closing device according to claim 15, wherein the narrowed space part is located on the proximal-side member.

* * * * *